US010533027B2

(12) United States Patent
Konno et al.

(10) Patent No.: US 10,533,027 B2
(45) Date of Patent: Jan. 14, 2020

(54) METHOD FOR PRODUCING CYCLOMETALATED IRIDIUM COMPLEX

(71) Applicants: TANAKA KIKINZOKU KOGYO K.K., Chiyoda-ku, Tokyo (JP); NATIONAL INSTITUTE OF ADVANCED INDUSTRIAL SCIENCE AND TECHNOLOGY, Chiyoda-ku, Tokyo (JP)

(72) Inventors: Hideo Konno, Tsukuba (JP); Junichi Taniuchi, Tsukuba (JP); Ryosuke Harada, Tsukuba (JP); Toshiyuki Shigetomi, Tsukuba (JP); Rumi Kobayashi, Tsukuba (JP); Yasushi Masahiro, Tokyo (JP)

(73) Assignees: TANAKA KIKINZOKU KOGYO K.K., Tokyo (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 16/060,105

(22) PCT Filed: Dec. 22, 2016

(86) PCT No.: PCT/JP2016/088394
§ 371 (c)(1),
(2) Date: Jun. 7, 2018

(87) PCT Pub. No.: WO2017/122516
PCT Pub. Date: Jul. 20, 2017

(65) Prior Publication Data
US 2018/0362565 A1 Dec. 20, 2018

(30) Foreign Application Priority Data

Jan. 14, 2016 (JP) ................. 2016-005255

(51) Int. Cl.
*C07F 15/00* (2006.01)
*C09K 11/06* (2006.01)
*H01L 51/00* (2006.01)
*H01L 51/50* (2006.01)

(52) U.S. Cl.
CPC .......... *C07F 15/0033* (2013.01); *C09K 11/06* (2013.01); *C09K 2211/1029* (2013.01); *C09K 2211/1044* (2013.01); *C09K 2211/1059* (2013.01); *C09K 2211/185* (2013.01); *H01L 51/0085* (2013.01); *H01L 51/5016* (2013.01)

(58) Field of Classification Search
CPC ................ C07F 15/0033; C09K 11/06; C09K 211/1029; C09K 211/1044; C09K 211/1059; C09K 211/185; H01L 51/0085; H01L 51/5016
See application file for complete search history.

(56) References Cited

U.S. PATENT DOCUMENTS

| | | | |
|---|---|---|---|
| 6,835,835 B1 | 12/2004 | Huo | |
| 2004/0253478 A1 | 12/2004 | Thompson et al. | |
| 2005/0288507 A1 | 12/2005 | Deaton | |
| 2006/0046095 A1 | 3/2006 | Ragini et al. | |
| 2006/0073358 A1 | 4/2006 | Lyu et al. | |
| 2006/0078760 A1 | 4/2006 | Ragini et al. | |
| 2006/0177695 A1 | 8/2006 | Ragini et al. | |
| 2006/0228582 A1 | 10/2006 | Ragini et al. | |
| 2007/0009759 A1 | 1/2007 | Burn et al. | |
| 2007/0190358 A1 | 8/2007 | Byun et al. | |
| 2008/0015355 A1 | 1/2008 | Schafer et al. | |
| 2008/0255361 A1 | 10/2008 | Matsuo et al. | |
| 2009/0062560 A1 | 3/2009 | Pretot et al. | |
| 2011/0034699 A1 | 2/2011 | Fuchs et al. | |
| 2011/0284799 A1 | 11/2011 | Stoessel et al. | |
| 2013/0119354 A1 | 5/2013 | Ma et al. | |
| 2013/0331577 A1 | 12/2013 | Van Pee et al. | |
| 2016/0326198 A1 | 11/2016 | Konno et al. | |

FOREIGN PATENT DOCUMENTS

| | | |
|---|---|---|
| CN | 1803815 A | 7/2006 |
| JP | 2001-106536 A | 4/2001 |
| JP | 2002-540572 A | 11/2002 |
| JP | 2005-516040 A | 6/2005 |
| JP | 2006-063080 A | 3/2006 |

(Continued)

OTHER PUBLICATIONS

PCT, International Search Report for PCT/JP2016/088394, dated Mar. 28, 2017.
Li et al., Acid induced acetylacetonato replacement in biscyclometalated iridium(III) complexes, Dalton Transactions, 2012, vol. 41, pp. 3807-3816, ISSN 1477-9226.
Konno et al., Selective One-pot Synthesis of Facial Tris-ortho-metalated Iridium(III) Complexes Using Microwave Irradiation, Chemistry Letters, 2003, vol. 32, No. 3, pp. 252-253, ISSN 0366-7022.
King et al., Excited-State Properties of a Triply Ortho-Metalated Iridium(III) Complex, J. Am. Chem. Soc., 1985, 107, 1431-1432.
Zhang et al., A New Synthetic Route to the Preparation of a Series of Strong Photoreducing Agents: fac Tris-Ortho-Metalated Complexes of Iridium(III) with Substituted 2-Phenylpyridines, Inorg. Chem. 1991, 30, 1685-1687.

*Primary Examiner* — Timothy R Rozof
(74) *Attorney, Agent, or Firm* — Orrick, Herrington & Sutcliffe LLP; Joseph A. Calvaruso; K. Patrick Herman

(57) ABSTRACT

The present invention provides a method for producing a cyclometalated iridium complex by use of a non-chlorine iridium raw material. The method for producing a cyclometalated iridium complex includes producing a cyclometalated iridium complex by reacting a raw material including an iridium compound with an aromatic heterocyclic bidentate ligand capable of forming an iridium-carbon bond, the raw material being non-halogenated iridium having a conjugated base of a strong acid as a ligand. Here, the non-halogenated iridium is preferably one containing a conjugated base of a strong acid having a pKa of 3 or less as a ligand.

19 Claims, No Drawings

(56) References Cited

FOREIGN PATENT DOCUMENTS

| | | |
|---|---|---|
| JP | 2006-104201 A | 4/2006 |
| JP | 2006-111623 A | 4/2006 |
| JP | 2006-213723 A | 8/2006 |
| JP | 2006-290891 A | 10/2006 |
| JP | 2006-523231 A | 10/2006 |
| JP | 2007-504272 A | 3/2007 |
| JP | 2007-091718 A | 4/2007 |
| JP | 2007-513158 A | 5/2007 |
| JP | 2007-224025 A | 9/2007 |
| JP | 2008-504342 A | 2/2008 |
| JP | 2008-505076 A | 2/2008 |
| JP | 2008-514005 A | 5/2008 |
| JP | 2009-522228 A | 6/2009 |
| JP | 2009-526071 A | 7/2009 |
| JP | 2009-541431 A | 11/2009 |
| JP | 2009-544167 A | 12/2009 |
| JP | 2012/006914 A | 1/2012 |
| JP | 2013-103938 A | 5/2013 |
| JP | 2014-005223 A | 1/2014 |
| JP | 2014-505041 A | 2/2014 |
| JP | 2015-189687 A | 11/2015 |
| WO | WO 2000/057676 A1 | 9/2000 |
| WO | WO 2002/002714 A2 | 1/2002 |
| WO | WO 2003/063555 A1 | 7/2003 |
| WO | WO 2005/056567 A1 | 6/2005 |
| WO | WO 2006/033857 A2 | 3/2006 |
| WO | WO 2007/032203 A1 | 3/2007 |
| WO | WO 2007/095118 A2 | 8/2007 |
| WO | WO 2008010915 A2 | 1/2008 |
| WO | WO 2009/011447 A2 | 1/2009 |
| WO | WO 2010/086089 A1 | 8/2010 |
| WO | WO 2013/163019 A1 | 10/2013 |
| WO | WO2013/163019 A1 * | 10/2013 |
| WO | WO 2013/163022 A1 | 10/2013 |
| WO | WO 2013/165118 A1 | 11/2013 |
| WO | WO 2015/104961 A1 | 7/2015 |

\* cited by examiner

METHOD FOR PRODUCING CYCLOMETALATED IRIDIUM COMPLEX

TECHNICAL FIELD

The present invention relates to a technique for producing a cyclometalated iridium complex applicable to organic electroluminescent (EL) devices, organic electrochemiluminescent (ECL) devices, luminescent sensors, photosensitizing pigments, photocatalysts, various light sources and the like.

BACKGROUND ART

"Cyclometalated iridium complex" is a general term for organic iridium complexes, in which multidentate ligands are coordinated to the iridium atom to form a ring, and at least one iridium-carbon bond is present, for example, tris(2-phenylpyridine)iridium (Ir(ppy)$_3$) (Chemical Formula 1). Among cyclometalated iridium complexes, those coordinated with an aromatic heterocyclic bidentate ligand such as a 2-phenylpyridine derivative or a 1-phenylisoquinoline derivative as in Chemical Formula 1 are used as phosphorescent materials for organic EL devices and the like. Organic EL devices obtained by use of a phosphorescent material have light-emitting efficiency 3 to 4 times higher than that of organic EL devices obtained by use of a conventional fluorescent material, and thus are essential to achieve higher efficiency/energy saving in organic EL devices.

[Chemical Formula 1]

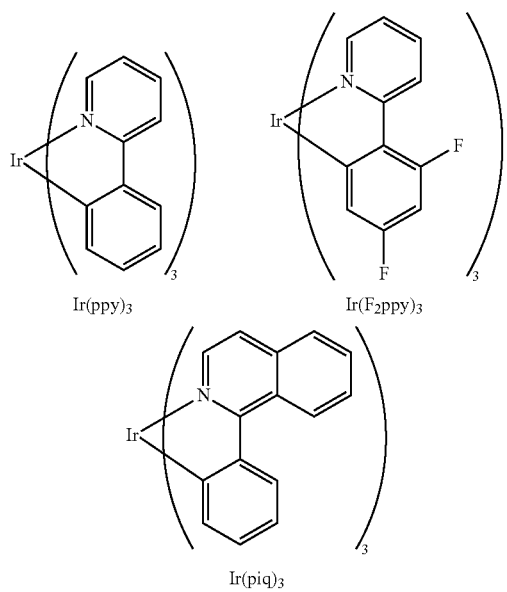

Ir(ppy)$_3$        Ir(F$_2$ppy)$_3$

Ir(piq)$_3$

Examples of the cyclometalated iridium complex include a biscyclometalated iridium complex, in which two aromatic heterocyclic bidentate ligands are coordinated to the iridium atom, and a triscyclometalated iridium complex, in which three aromatic heterocyclic bidentate ligands are coordinated to the iridium atom. Among them, triscyclometalated iridium complexes have particularly high thermal stability and, when applied to, for example, organic EL devices are expected to increase the life.

Examples of the method for producing a cyclometalated iridium complex as shown above include a method in which the cyclometalated iridium complex is synthesized in a single step by reacting iridium trichloride with an aromatic heterocyclic bidentate ligand such as 2-phenylpyridine (ppy) (Chemical Formula 2, Non-Patent Document 1).

[Chemical Formula 2]

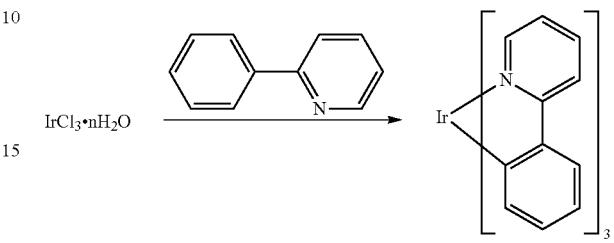

However, in the method for producing a cyclometalated iridium complex in Non-Patent Document 1, a chlorine-crosslinked dimer (Chemical Formula 3) is obtained, and a desired cyclometalated iridium complex cannot be synthesized with a high yield. Further, a cyclometalated iridium complex obtained by single-step synthesis with iridium trichloride used as a raw material has the problem that a chlorine component derived from iridium trichloride remains. It has been pointed out that such a remaining chlorine component adversely affects the light-emitting properties when applied to an organic EL device (see Patent Document 1).

[Chemical Formula 3]

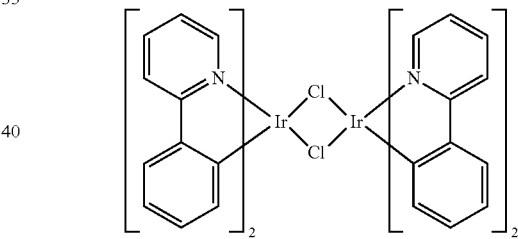

In addition, as another example of a method for producing a cyclometalated iridium complex, a method is known in which a cyclometalated iridium complex is obtained in a single step by reacting tris(2,4-pentanedionato)iridium(III) (hereinafter, also referred to as Ir(acac)$_3$) with an aromatic heterocyclic bidentate ligand such as 2-phenylpyridine (ppy) (Chemical Formula 4, Non-Patent Document 2).

[Chemical Formula 4]

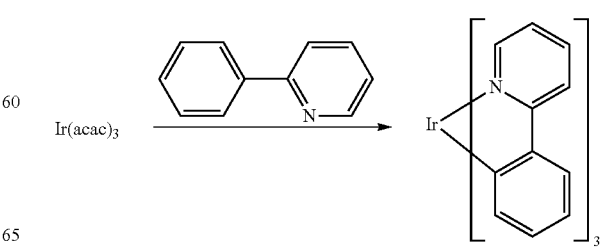

The production method described in Non-Patent Document 2 uses, as a raw material, Ir(acac)$_3$ that is a non-chlorine iridium raw material, and has an advantage that a chlorine component derived from an iridium raw material does not remain in a cyclometalated iridium complex as a product. However, Ir(acac)$_3$ is thermally stable, and has low reactivity, and thus has the problem that the synthesis yield of the cyclometalated iridium complex is low.

The problem about a synthesis yield will be described in detail below. Since Ir(acac)$_3$ is thermally stable, in order to obtain a cyclometalated iridium complex in good yield, generally, the synthesis is performed under high-temperature conditions at 200° C. or more. Thus, sometimes, an unexpected decomposition reaction proceeds, and the yield or purity was decreased.

Examples of the method for producing a cyclometalated iridium complex further include a method in which a cyclometalated iridium complex is synthesized in a single step by reacting iridium acetate with an aromatic heterocyclic bidentate ligand (Chemical Formula 5, Patent Document 2).

[Chemical Formula 5]

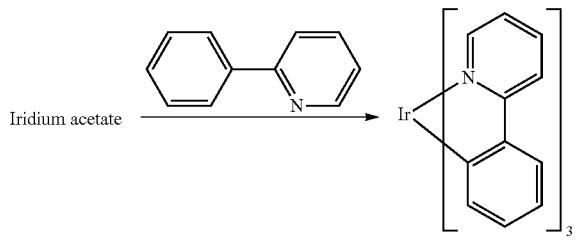

Iridium acetate as a non-chlorine iridium raw material has reaction activity, and is capable of producing a cyclometalated iridium complex even at a reaction temperature of 200° C. or lower. Therefore, there is a low possibility that in a reaction under high-temperature conditions, an unexpected decomposition reaction proceeds, resulting in yield reduction. In addition, since a non-chlorine iridium raw material is used, a chlorine component does not remain.

However, the method for producing a cyclometalated iridium complex with iridium acetate used as a raw material has a problem. This problem will be described in detail below. For a triscyclometalated iridium complex, which is particularly suitable as a phosphorescent material for organic EL devices etc., among cyclometalated iridium complexes, a facial isomer and a meridional isomer are present as geometric isomers. Among these isomers, the facial isomer is known to have high light-emitting efficiency, thus being desirable as a light-emitting material. The present inventors have found that when a triscyclometalated iridium complex is produced with iridium acetate used as a raw material, a meridional isomer undesirable as a light-emitting material tends to be easily produced.

RELATED ART DOCUMENT

Patent Documents

Patent Document 1: WO 07/032203 A1
Patent Document 2: JP 2012-6914 A

Non-Patent Documents

Non-Patent Document 1: J. Am Chem. Soc., Vol. 107, p. 1431, 1985

Non-Patent Document 2: Inorg. Chem., Vol. 30, p. 1685, 1991

SUMMARY OF THE INVENTION

Problems to be Solved by the Invention

In view of the above background, an object of the present invention is to provide a technique which ensures that a cyclometalated iridium complex to be suitably used as a light-emitting material for an organic EL device etc. can be obtained with a high purity from a non-chlorine iridium raw material by a single-step synthesis reaction at lower temperature. In particular, a method that makes it easy to produce a facial isomer in production of a triscyclometalated iridium complex is disclosed.

Means for Solving the Problems

In order to solve the above-described problems, the present inventors have extensively conducted studies on an iridium raw material for developing a method for producing a cyclometalated iridium complex from a non-chlorine iridium raw material by a single-step. As a result of the studies, the present inventors have found that the above-described problems can be solved by applying, as a non-chlorine iridium raw material, non-halogenated iridium having a conjugated base of a strong acid as a ligand.

It has been heretofore considered that when in a reaction of an iridium compound with an aromatic heterocyclic bidentate ligand, presence of a strong acid in a reaction system should be avoided. This is because it has been considered that when a strong acid such as hydrochloric acid is generated as a by-product in formation of an iridium-carbon bond, a cyclometalation reaction is hindered, leading to a considerable reduction in yield of a desired cyclometalated iridium complex.

On the other hand, the present inventors have found that use of non-halogenated iridium having as a ligand a conjugated base of a strong acid, which has not been heretofore used, makes it possible to obtain a cyclometalated iridium complex with a high yield by a single-step even in the presence of a strong acid.

In addition, the present inventors have found that as compared to a case where iridium acetate being a conventional non-chlorine iridium raw material is used, a cyclometalated iridium complex as a facial isomer suitable as a phosphorescent material for an organic EL device can be produced with a higher purity, and thus the present invention has been made.

The above findings indicate unforeseen phenomena that have not been heretofore known at all, and these findings are novel ones that have been obtained only by constantly conducting many minute experiments by the present inventors. On the basis of these findings, the present inventors have conceived the present invention capable of solving the above-described problems.

That is, the present invention provides a method for producing a cyclometalated iridium complex, the method including producing a cyclometalated iridium complex by reacting a raw material including an iridium compound with an aromatic heterocyclic bidentate ligand capable of forming an iridium-carbon bond, the raw material being non-halogenated iridium having a conjugated base of a strong acid as a ligand.

Hereinafter, the method for producing a cyclometalated iridium complex according to the present invention will be described in detail. First, non-halogenated iridium having a conjugated base of a strong acid as a ligand, which is to be used in the present invention, will be described.

The non-halogenated iridium having a conjugated base of a strong acid as a ligand is an iridium compound which has a conjugated base of a strong acid as a ligand, and is not halogenated iridium. Here, examples of the halogenated iridium that is excluded in the present invention include iridium compounds as described in JP 2015-189687 A, JP 2014-005223 A, JP 2007-091718 A, JP 2014-505041 W, JP 2007-513159 W and so on. Specific examples of the halogenated iridium include iridium chloride (III), iridium bromide (III), iridium iodide (III), iridium chloride (IV) acid, iridium bromide (IV) acid, iridium iodate (IV) acid, and salts (ammonium salts, potassium salts, sodium salts and the like) and hydrates of these compounds.

The strong acid is an acid having a pKa of 3 or less, preferably an acid having a pKa of 2 or less, more preferably an acid having a pKa of 1 or less. Examples of the acid include nitric acid, sulfuric acid, trifluoroacetic acid, arylsulfonic acids (p-toluenesulfonic acid, benzenesulfonic acid and the like), perfluoroalkylsulfonic acids (trifluoromethanesulfonic acid, nonafluorobutanesulfonic acid and the like), and alkylsulfonic acids (methanesulfonic acid, ethanesulfonic acid, butanesulfonic acid and the like). Among these acids, nitric acid or sulfuric acid is preferable, with nitric acid being more preferable.

Specific examples of the non-halogenated iridium having a conjugated base of a strong acid as a ligand include iridium nitrate, iridium sulfate, iridium trifluoroacetate, iridium p-toluenesulfonate, iridium benzenesulfonate, iridium trifluoromethanesulfonate, iridium nonafluorobutanesulfonate, iridium methanesulfonate, iridium ethanesulfonate and iridium butanesulfonate, and iridium nitrate or iridium sulfate is preferable, with iridium nitrate being more preferable.

The iridium in non-halogenated iridium having a conjugated base of a strong acid as a ligand is preferably trivalent or tetravalent, more preferably tetravalent. The iridium may be a mixture of trivalent iridium and tetravalent iridium.

Examples of the iridium nitrate that can be suitably used in the present invention include iridium nitrates represented by $Ir(NO_3)_3$ and $Ir(NO_3)_4$, and any of these iridium nitrates or a mixture of these iridium nitrates can be applied. In addition, the cyclometalated iridium complex may contain an iridium compound having as a ligand a hydroxide ion represented by $[Ir(NO_3)_2(OH)_2]$, $[Ir(NO_3)_2(OH)_2]$, $[Ir(NO_3)_2(H_2O)_2]^+$ or $[Ir(NO_3)_2(H_2O)_2]^{2+}$ or water. Further, the cyclometalated iridium complex may contain a polynuclear iridium compound crosslinked with a hydroxide ion ligand represented, for example by $[(NO_3)_2Ir(OH)_2 Ir(NO_3)_2]$. As a preferred method for producing indium nitrate, mention is made of, for example, a method in which iridium nitrate is produced by way of iridium hydroxide as described in JP 2001-106536 A.

An example of a structure of iridium sulfate to be suitably used in the present invention is $Ir_2(SO_4)_3$, $Ir(SO_4)_2$.

Non-halogenated iridium having a conjugated base of a strong acid as a ligand, which is used in the method for producing a cyclometalated iridium complex according to the present invention, can be used in a solid state. The solid state is not particularly limited, and examples thereof include a lump form, a small piece form and a particle form. In addition, when the non-halogenated iridium is solid, the non-halogenated iridium may contain crystal water or a crystal solvent.

In addition, non-halogenated iridium having a conjugated base of a strong acid as a ligand, which is used in the present invention, may be dissolved or dispersed in a solvent such as water or alcohol. As a solvent here, water is especially preferable, and it is more preferable that non-halogenated iridium is dissolved or dispersed in water.

Particularly, when non-halogenated iridium having a conjugated base of a strong acid as a ligand is used in the form of an aqueous solution, the aqueous solution is preferably a strong-acidic solution having a pH of 0 to 3. This is because when the pH is more than 3, a precipitate ($IrO_2.nH_2O$) may be gradually generated with elapse of time. It is also preferable that the pH of a solution containing non-halogenated iridium having a conjugated base of a strong acid as a ligand is adjusted by appropriately adding a base (sodium hydroxide, potassium hydroxide, sodium hydrogen carbonate or the like) according to the properties of a phosphorescent material to be produced.

The iridium concentration of a solution containing non-halogenated iridium having a conjugated base of a strong acid as a ligand is preferably 0.01 to 99.9 wt %, more preferably 0.1 to 90 wt %, especially preferably 1 to 70 wt %, still more preferably 5 to 50 wt %.

The concentration of a residual halogen contained in non-halogenated iridium having a conjugated base of a strong acid as a ligand is preferably 1000 ppm or less, more preferably 100 ppm or less, especially preferably 10 ppm or less.

An aromatic heterocyclic bidentate ligand to be reacted with an iridium compound raw material in the present invention will now be described. The aromatic heterocyclic bidentate ligand to be used in the present invention is an aromatic heterocyclic bidentate ligand capable of forming an iridium-carbon bond. The aromatic heterocyclic bidentate ligand is preferably an aromatic heterocyclic bidentate ligand that forms one iridium-nitrogen bond and one iridium-carbon bond or an aromatic heterocyclic bidentate ligand that forms two iridium-carbon bonds, more preferably an aromatic heterocyclic bidentate ligand that forms one iridium-nitrogen bond and one iridium-carbon bond.

Specifically, the aromatic heterocyclic bidentate ligand is an aromatic heterocyclic bidentate ligand represented by the general formula (1). In the present invention, a cyclometalated iridium complex represented by the general formula (2) can be produced by reacting non-halogenated iridium having a conjugated base of a strong acid as a ligand as described above with an aromatic heterocyclic bidentate ligand represented by the general formula (1).

[Chemical Formula 6]

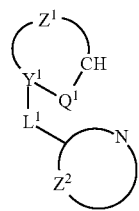

General formula (1)

[Chemical Formula 7]

General formula (2)

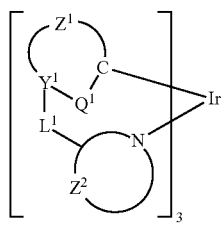

(in general formulae (1) and (2), N represents a nitrogen atom; C represents a carbon atom; $Z^1$ and $Z^2$ each independently represent a nonmetal atom group necessary for forming a 5- or 6-membered ring; the formed ring may further form a fused ring with another ring; $L^1$ represents a single bond or a divalent group; $Y^1$ represents a nitrogen atom or a carbon atom; $Q^1$ represents a linkage of a carbon atom with $Y^1$ through a single bond when $Y^1$ is a nitrogen atom; and $Q^1$ represents a linkage of a carbon atom with $Y^1$ through a double bond when $Y^1$ is a carbon atom.)

In addition, in the present invention, a cyclometalated iridium complex represented by the general formula (4) can be produced by reacting non-halogenated iridium having a conjugated base of a strong acid as a ligand as described above, an aromatic heterocyclic bidentate ligand represented by the general formula (1) and an aromatic heterocyclic bidentate ligand represented by the general formula (3).

[Chemical Formula 8]

General formula (3)

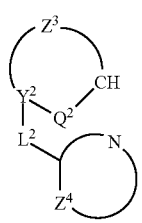

[Chemical Formula 9]

General formula (4)

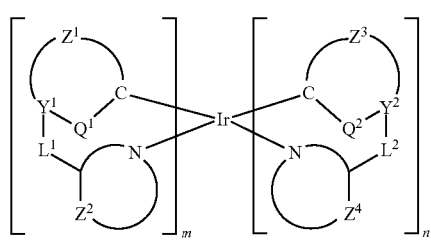

(in general formulae (3) and (4), N represents a nitrogen atom; C represents a carbon atom; $Z^1$ and $Z^2$ each independently represent a nonmetal atom group necessary for forming a 5- or 6-membered ring; the formed ring may further form a fused ring with another ring; $L^1$ represents a single bond or a divalent group; $Y^1$ represents a nitrogen atom or a carbon atom; $Q^1$ represents a linkage of a carbon atom with $Y^1$ through a single bond when $Y^1$ is a nitrogen atom; $Q^1$ represents a linkage of a carbon atom with $Y^1$ through a double bond when $Y^1$ is a carbon atom; $Z^3$ and $Z^4$ each independently represent a nonmetal atom group necessary for forming a 5- or 6-membered ring; the formed ring may further form a fused ring with another ring; $L^2$ represents a single bond or a divalent group; $Y^2$ represents a nitrogen atom or a carbon atom; $Q^2$ represents a linkage of a carbon atom with $Y^2$ through a single bond when $Y^2$ is a nitrogen atom; $Q^2$ represents a linkage of a carbon atom with $Y^2$ through a double bond when $Y^2$ is a carbon atom; the aromatic heterocyclic bidentate ligand represented by the general formula (1) is not identical to the aromatic heterocyclic bidentate ligand represented by the general formula (3); and m is 1 or 2, and n is 1 or 2, with the proviso that m+n=3.)

Examples of the specific structure of the aromatic heterocyclic bidentate ligand to be used in the present invention include structures shown by the following structure examples 1 to 3. In addition, mention is made of structures represented by general formulae (5) to (12). Aromatic heterocyclic bidentate ligands having structures represented by the general formulae (5) to (12) are preferable, and among them, those having a structure represented by the general formula (5), (7), (10) or (11) are more preferable, and those having a structure represented by the general formula (5), (7) or (10) are especially preferable. In the structure examples 1 to 3 and General Formulae (5) to (12), * indicates a site of bonding to iridium.

[Chemical Formula 10]

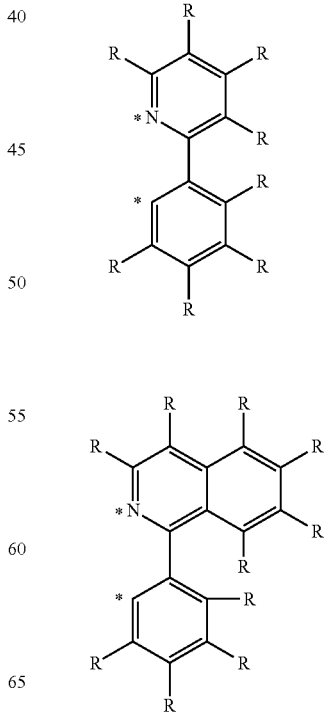
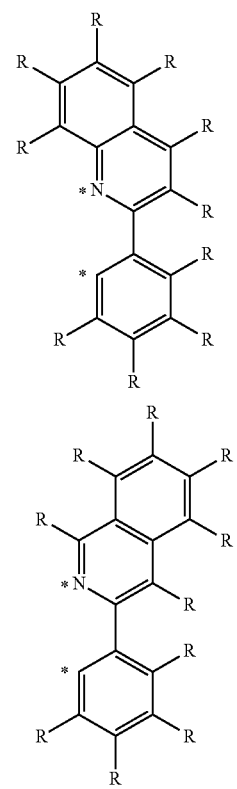

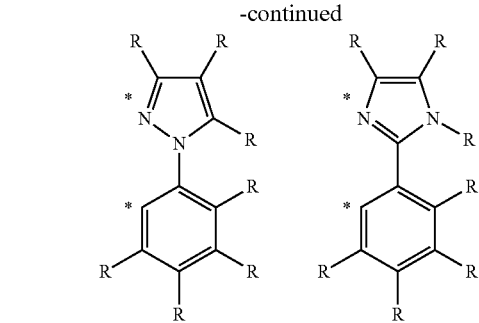
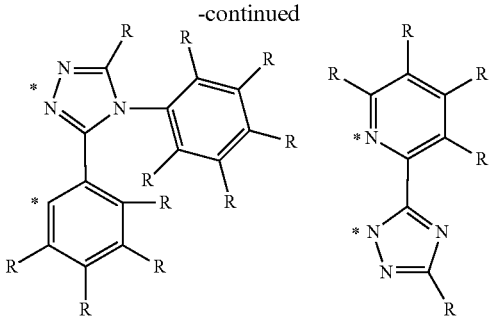
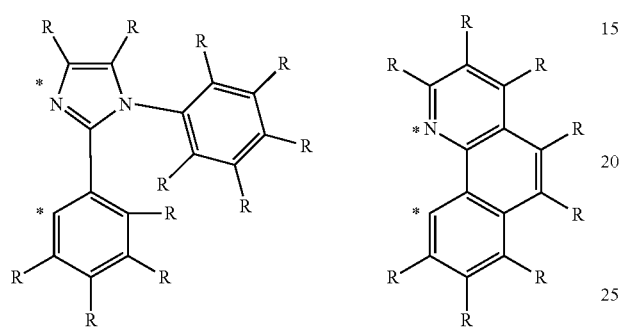
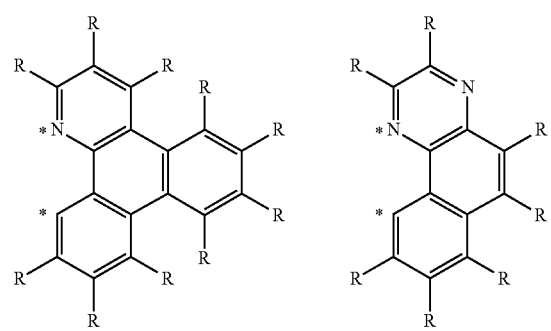
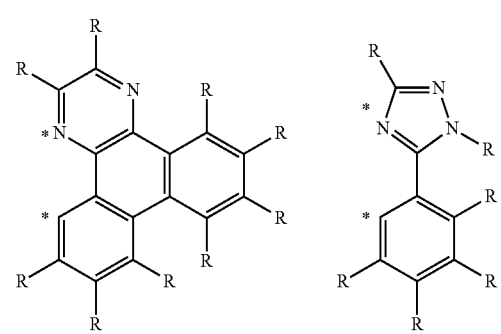
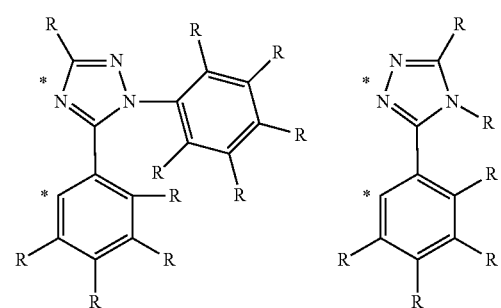
Structure Example 1 of Aromatic Heterocyclic Bidentate Ligand
[Chemical Formula 11]
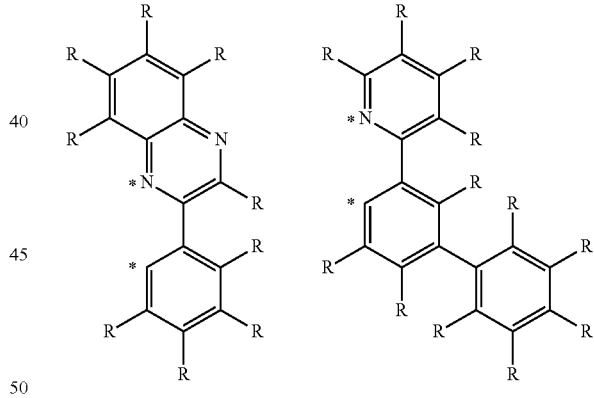
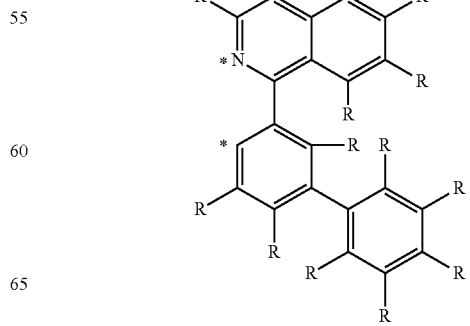

-continued
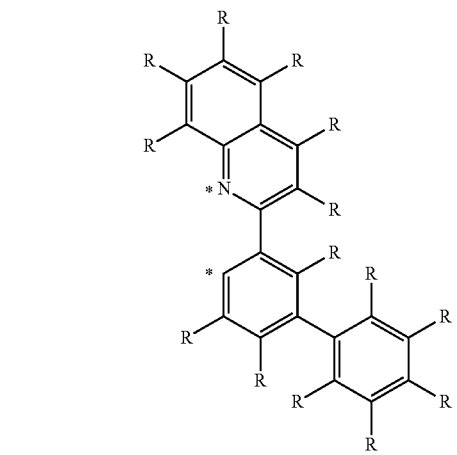
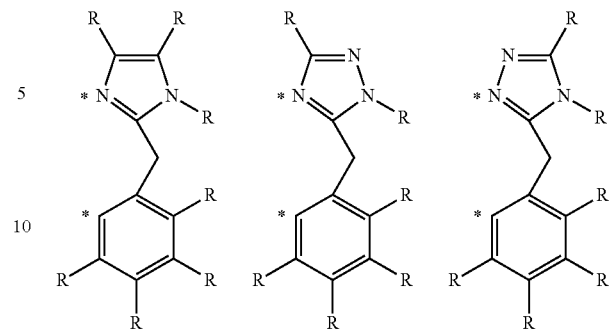
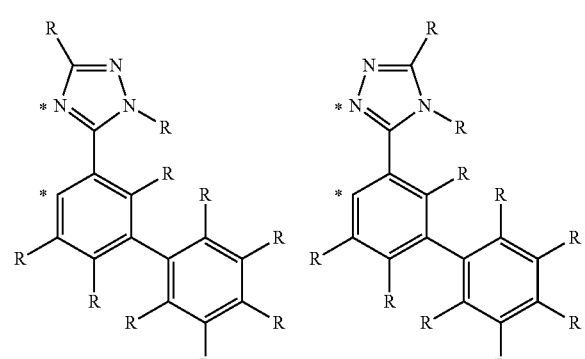
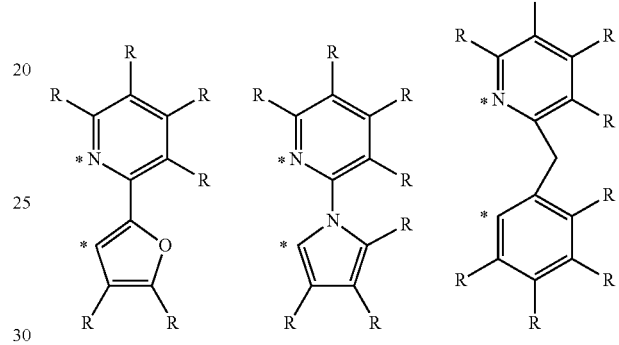
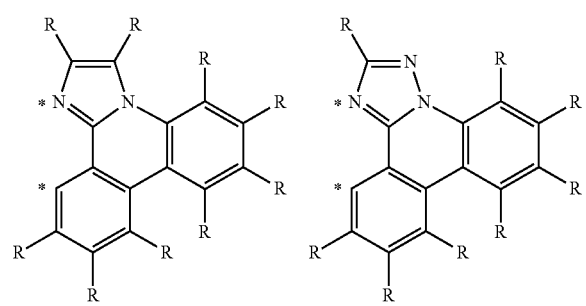
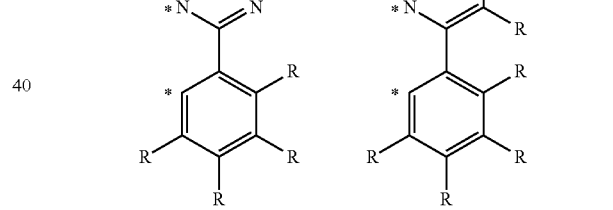
Structure Example 2 of Aromatic Heterocyclic Bidentate Ligand
[Chemical Formula 12]
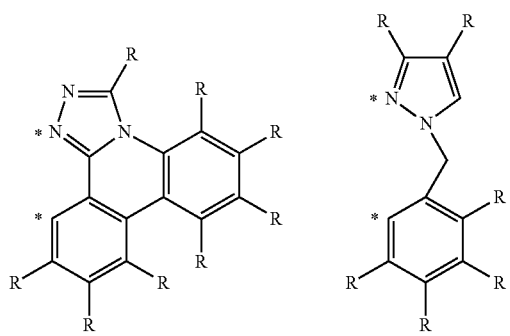
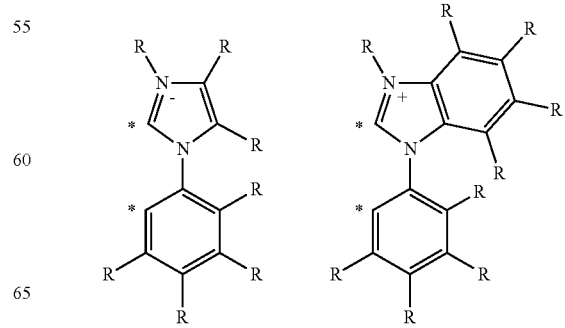

-continued
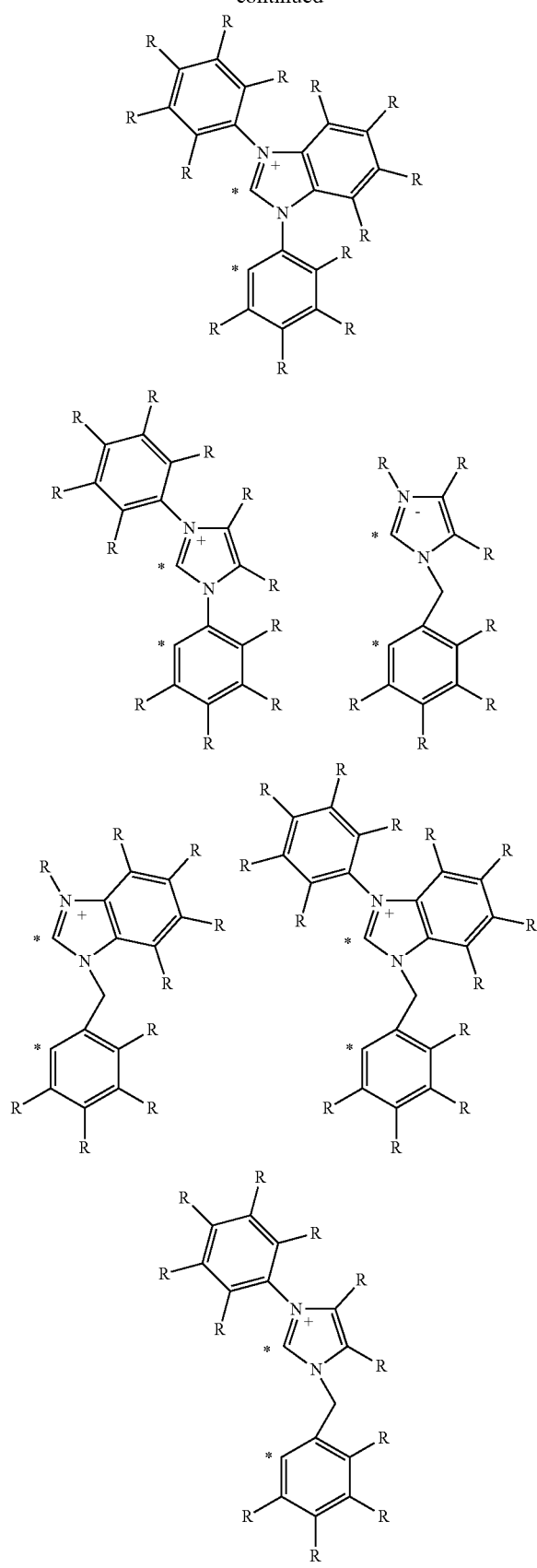
Structure Example 3 of Aromatic Heterocyclic Bidentate Ligand
[Chemical Formula 13]
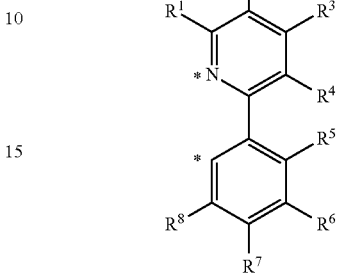
General formula (5)
[Chemical Formula 14]
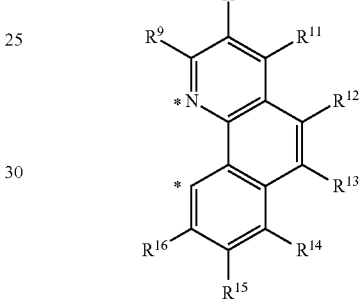
General formula (6)
[Chemical Formula 15]
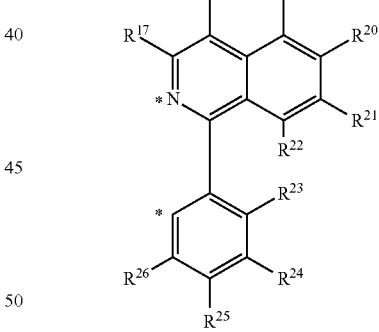
General formula (7)
[Chemical Formula 16]
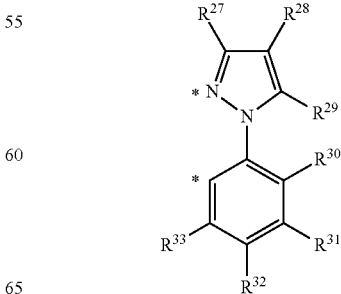
General formula (8)

[Chemical Formula 17]

General formula (9)

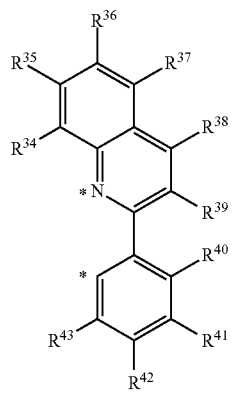

[Chemical Formula 18]

General formula (10)

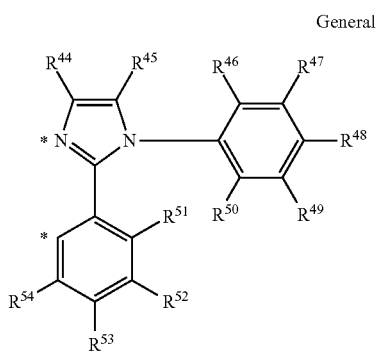

[Chemical Formula 19]

General formula (11)

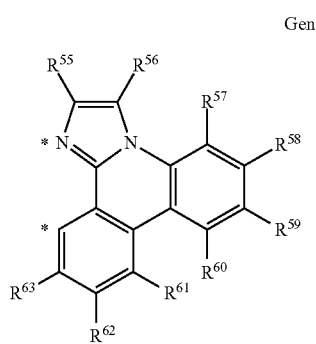

[Chemical Formula 20]

General formula (12)

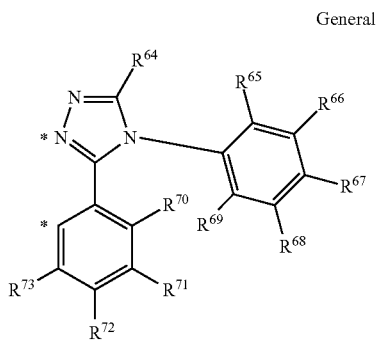

In the structure examples 1 to 3 and general formulae (5) to (12), R and $R^1$ to $R^{73}$ each represent a hydrogen atom or a substituent. Examples of the substituent include the following substituents.

Alkyl groups (having preferably 1 to 30, more preferably 1 to 20, especially preferably 1 to 10 carbon atoms) (e.g. methyl, ethyl, iso-propyl, tert-butyl, n-octyl, n-decyl, n-hexadecyl, cyclopropyl, cyclopentyl and cyclohexyl).

Alkenyl groups (having preferably 2 to 30, more preferably 2 to 20, especially preferably 2 to 10 carbon atoms) (e.g. vinyl, allyl, 2-butenyl and 3-pentenyl).

Alkynyl groups (having preferably 2 to 30, more preferably 2 to 20, especially preferably 2 to 10 carbon atoms) (e.g. propargyl and 3-pentynyl).

Aryl groups (having preferably 6 to 30, more preferably 6 to 20, especially preferably 6 to 12 carbon atoms) (e.g. phenyl, p-methylphenyl, naphthyl and anthranil).

Amino groups (having preferably 0 to 30, more preferably 0 to 20, especially preferably 0 to 10 carbon atoms) (e.g. amino, methylamino, dimethylamino, diethylamine, dibenzylamino, diphenylamino and ditolylamino).

Alkoxy groups (having preferably 1 to 30, more preferably 1 to 20, especially preferably 1 to 10 carbon atoms) (e.g. methoxy, ethoxy, butoxy and 2-ethylhexyloxy).

Aryloxy groups (having preferably 6 to 30, more preferably 6 to 20, especially preferably 6 to 12 carbon atoms) (e.g. phenyloxy, 1-naphthyloxy and 2-naphthyloxy).

Heterocyclic oxy groups (having preferably 1 to 30, more preferably 1 to 20, especially preferably 1 to 12 carbon atoms) (e.g. pyridyloxy, pyrazyloxy, pyrimidyloxy and quinolyloxy).

Acyl groups (having preferably 1 to 30, more preferably 1 to 20, especially preferably 1 to 12 carbon atoms) (e.g. acetyl, benzoyl, formyl and pivaloyl).

Alkoxycarbonyl groups (having preferably 2 to 30, more preferably 2 to 20, especially preferably 2 to 12 carbon atoms) (e.g. methoxycarbonyl and ethoxycarbonyl).

Aryloxycarbonyl groups (having preferably 7 to 30, more preferably 7 to 20, especially preferably 7 to 12 carbon atoms) (e.g. phenyloxycarbonyl).

Acyloxy groups (having preferably 2 to 30, more preferably 2 to 20, especially preferably 2 to 10 carbon atoms) (e.g. acetoxy and benzoyloxy).

Acylamino groups (having preferably 2 to 30, more preferably 2 to 20, especially preferably 2 to 10 carbon atoms) (e.g. acetylamino and benzoylamino).

Alkoxycarbonylamino groups (having preferably 2 to 30, more preferably 2 to 20, especially preferably 2 to 12 carbon atoms) (e.g. methoxycarbonylamino).

Aryloxycarbonylamino groups (having preferably 7 to 30, more preferably 7 to 20, especially preferably 7 to 12 carbon atoms) (e.g. phenyloxycarbonylamino).

Sulfonylamino groups (having preferably 1 to 30, more preferably 1 to 20, especially preferably 1 to 12 carbon atoms) (e.g. methanesulfonylamino and benzenesulfonylamino).

Sulfamoyl groups (having preferably 0 to 30, more preferably 0 to 20, especially preferably 0 to 12 carbon atoms) (e.g. sulfamoyl, methylsulfamoyl, dimethylsulfamoyl and phenylsulfamoyl).

Carbamoyl groups (having preferably 1 to 30, more preferably 1 to 20, especially preferably 1 to 12 carbon atoms) (e.g. carbamoyl, methylcarbamoyl, diethylcarbamoyl and phenylcarbamoyl).

Alkylthio groups (having preferably 1 to 30, more preferably 1 to 20, especially preferably 1 to 12 carbon atoms) (e.g. methylthio and ethylthio).

Arylthio groups (having preferably 6 to 30, more preferably 6 to 20, especially preferably 6 to 12 carbon atoms) (e.g. phenylthio).

Heterocyclic thio groups (having preferably 1 to 30, more preferably 1 to 20, especially preferably 1 to 12 carbon atoms) (e.g. pyridylthio, 2-benzimidazolylthio, 2-benzoxazolylthio and 2-benzthiazolylthio).

Sulfonyl groups (having preferably 1 to 30, more preferably 1 to 20, especially preferably 1 to 12 carbon atoms) (e.g. mesyl and tosyl).

Sulfinyl groups (having preferably 1 to 30, more preferably 1 to 20, especially preferably 1 to 12 carbon atoms) (e.g. methanesulfinyl and benzenesulfinyl).

Ureide groups (having preferably 1 to 30, more preferably 1 to 20, especially preferably 1 to 12 carbon atoms) (e.g. ureide, methylureide and phenylureide).

Phosphoramide groups (having preferably 1 to 30, more preferably 1 to 20, especially preferably 1 to 12 carbon atoms) (e.g. diethylphosphoramide and phenylphosphoramide).

Hydroxyl groups, mercapto groups, halogen atoms (e.g. fluorine atom, chlorine atom, bromine atom and iodine atom), cyano groups, sulfo groups, carboxyl groups, nitro groups, trifluoromethyl groups, hydroxamic acid groups, sulfino groups, hydrazino groups, imino groups and heterocyclic groups (having preferably 1 to 30, more preferably 1 to 12 carbon atoms and having a nitrogen atom, an oxygen atom or a sulfur atom as a heteroatom (specifically, imidazolyl, pyridyl, quinolyl, furyl, thienyl, piperidyl, morpholino, benzoxazolyl, benzimidazolyl, benzothiazolyl, carbazolyl group, azepinyl group and the like).

Silyl groups (having preferably 3 to 40, more preferably 3 to 30, especially preferably 3 to 24 carbon atoms) (e.g. trimethylsilyl and triphenylsilyl).

Silyloxy groups (having preferably 3 to 40, more preferably 3 to 30, especially preferably 3 to 24 carbon atoms) (e.g. trimethylsilyloxy and triphenylsilyloxy).

Among the above-mentioned substituents, alkyl groups, aryl groups, amino groups, alkoxy groups, aryloxy groups, halogen atoms, cyano groups, trifluoromethyl groups and heterocyclic groups are more preferable, alkyl groups, aryl groups, halogen atoms, cyano groups, trifluoromethyl groups and heterocyclic groups are especially preferable, and alkyl groups, aryl groups and halogen atoms are still more preferable. Among the above-mentioned substituents, those that are desirable are as described above, and these substituents may be further substituted with substituents defined by R and $R^1$ to $R^{73}$.

The aromatic heterocyclic bidentate ligand will be described in detail on the basis of the above-described structure formulae. Examples of the aromatic heterocyclic bidentate ligand include the following ligands. Specifically, a 2-phenylpyridine derivative, a 2-phenylquinoline derivative, a 1-phenylisoquinoline derivative, a 3-phenylisoquinoline derivative, a 2-(2-benzothiophenyl)pyridine derivative, a 2-thienylpyridine derivative, a 1-phenylpyrazole derivative, a 1-phenyl-1H-indazole derivative, a 2-phenylbenzothiazole derivative, a 2-phenylthiazole derivative, a 2-phenylbenzoxazole derivative, a 2-phenyloxazole derivative, a 2-furanylpyridine derivative, a 2-(2-benzofuranyl)pyridine derivative, a 7,8-benzoquinoline derivative, a 7,8-benzoquinoxaline derivative, a dibenzo[f,h]quinoline derivative, a dibenzo[f,h]quinoxaline derivative, a benzo[h]-5,6-dihydroquinoline derivative, a 9-(2-pyridyl)carbazole derivative, a 1-(2-pyridyl)indole derivative, a 1-(1-naphthyl)isoquinoline derivative, a 1-(2-naphthyl)isoquinoline derivative, a 2-(2-naphthyl)quinoline derivative, a 2-(1-naphthyl)quinoline derivative, a 3-(1-naphthyl)isoquinoline derivative, a 3-(2-naphthyl)isoquinoline derivative, a 2-(1-naphthyl)pyridine derivative, a 2-(2-naphthyl)pyridine derivative, a 6-phenylphenanthridine derivative, a 6-(1-naphthyl)phenanthridine derivative, a 6-(2-naphthyl)phenanthridine derivative, a benzo[c]acridine derivative, a benzo[c]phenazine derivative, a dibenzo[a,c]acridine derivative, a dibenzo[a,c]phenazine derivative, a 2-phenylquinoxaline derivative, a 2,3-diphenylquinoxaline derivative, a 2-benzylpyridine derivative, a 2-phenylbenzimidazole derivative, a 3-phenylpyrazole derivative, a 4-phenylimidazole derivative, a 2-phenylimidazole derivative, a 1-phenylimidazole derivative, a 4-phenyltriazole derivative, a 5-phenyltetrazole derivative, a 2-alkenylpyridine derivative, a 5-phenyl-1,2,4-triazole derivative, an imidazo[1,2-f]phenanthridine derivative, a 1-phenylbenzimidazolium salt derivative, and a 1-phenylimidazolium salt derivative are preferable.

Among them, as the aromatic heterocyclic bidentate ligand, a 2-phenylpyridine derivative, a 2-phenylquinoline derivative, a 1-phenylisoquinoline derivative, a 3-phenylisoquinoline derivative, a 1-phenylpyrazole derivative, a 7,8-benzoquinoline derivative, a 7,8-benzoquinoxaline derivative, a dibenzo[f,h]quinoline derivative, a dibenzo[f,h]quinoxaline derivative, a benzo[h]-5,6-dihydroquinoline derivative, a 6-phenylphenanthridine derivative, a 2-phenylquinoxaline derivative, a 2,3-diphenylquinoxaline derivative, a 2-phenylbenzimidazole derivative, a 3-phenylpyrazole derivative, a 4-phenylimidazole derivative, a 2-phenylimidazole derivative, a 1-phenylimidazole derivative, a 4-phenyltriazole derivative, a 5-phenyltetrazole derivative, a 5-phenyl-1,2,4-triazole derivative, an imidazo[1,2-f]phenanthridine derivative, a 1-phenylbenzimidazolium salt derivative, and a 1-phenylimidazolium salt derivative are more preferable. In addition, a 2-phenylpyridine derivative, a 7,8-benzoquinoxaline derivative, a 1-phenylisoquinoline derivative, a 1-phenylpyrazole derivative, a 2-phenylimidazole derivative, a 5-phenyl-1,2,4-triazole derivative and a 1,2-imidazo[f]phenanthridine derivative are especially preferable, and a 2-phenylpyridine derivative, a 1-phenylisoquinoline derivative, a 2-phenylimidazole derivative and an imidazo[1,2-f]phenanthridine derivative are still more preferable.

In the method for producing a cyclometalated iridium complex according to the present invention, non-halogenated iridium having a conjugated base of a strong acid as a ligand as described above is reacted with the above-mentioned aromatic heterocyclic bidentate ligand.

The above reaction may be carried out in air or an inert gas (nitrogen, argon, etc.) atmosphere, and is preferably performed in an inert gas atmosphere.

In addition, in the present invention, in order for the above reaction to proceed more smoothly, a solvent may be added to the reaction system of the synthesis reaction.

Examples of the solvent to be added to the reaction system include various kinds of organic solvents, such as saturated aliphatic hydrocarbons, halogenated aliphatic hydrocarbons, ketones, amides, esters, aromatic hydrocarbons, halogenated aromatic hydrocarbons, nitrogen-containing aromatic compounds, ethers, nitryls, alcohols, and ionic liquids, and alcohols (having preferably 1 to 30, more preferably 1 to 20, especially preferably 1 to 30 carbon atoms). Specific examples include ethylene glycol, diethylene glycol, triethylene glycol, tetraethylene glycol, 2-methoxyethanol, 2-ethoxyethanol, 1,2-propanediol, 1,3-propanediol and 1,3-butanediol. Among them, ethylene glycol, diethylene glycol, triethylene glycol, 1,2-propanediol, 1,3-propanediol and 1,3-butanediol are preferable. In addition, using a mixed solvent containing two or more kinds of the above solvents is also preferable.

The above-mentioned solvent is preferably one having a boiling point of 100° C. to 400° C., more preferably one having a boiling point of 150° C. to 350° C., especially preferably one having a boiling point of 180° C. to 300° C. at ambient pressure.

In production of a cyclometalated iridium complex, the concentration of non-halogenated iridium having a conjugated base of a strong acid as a ligand in the reaction system is not particularly limited, but is preferably 0.001 mol/L to 10.0 mol/L, more preferably 0.001 mol/L to 1.0 mol/L, especially preferably 0.01 mol/L to 1.0 mol/L, and most preferably 0.05 mol/L to 0.5 mol/L.

In production of a cyclometalated iridium complex, the reaction temperature is preferably 100° C. to 300° C., more preferably 150° C. to 250° C., especially preferably 160° C. to 220° C., especially preferably 170° C. to 200° C. In the present invention, a cyclometalated iridium complex can be synthesized even at a low temperature of 200° C. or lower.

In production of a cyclometalated iridium complex, the reaction time is preferably 1 to 100 hours, more preferably 3 to 80 hours, and especially preferably 5 to 50 hours.

In production of a cyclometalated iridium complex, the heating method is not particularly limited. Specifically, external heating using an oil bath, a sand bath, a mantle heater, a block heater, or a heat-circulation jacket, as well as heating by irradiation with microwaves can be utilized, for example.

The synthesis of a cyclometalated iridium complex is usually performed at ambient pressure, but may also be performed under increased pressure or reduced pressure as necessary.

In synthesis of a cyclometalated iridium complex, the amount of aromatic heterocyclic bidentate ligand used is not particularly limited, but is preferably 3 to 100 times, more preferably 3 to 50 times, especially preferably 3 to 30 times, and most preferably 3 to 10 times the molar amount of non-halogenated iridium having a conjugated base of a strong acid as a ligand.

The cyclometalated iridium complex obtained by the synthesis method described above is treated by a general post-treatment method and then, after purification as necessary or without purification, can be used as a high-purity product. As the method for post-treatment, for example, extraction, cooling, crystallization by adding water or an organic solvent, distillation of the solvent from the reaction mixture, and like operations may be performed alone or in combination. As the method for purification, recrystallization, distillation, sublimation, column chromatography, and the like may be performed alone or in combination.

The method for producing a cyclometalated iridium complex according to the present invention is suitable for production of a biscyclometalated iridium complex or a triscyclometalated iridium complex. Particularly, the method is suitable for production of a triscyclometalated iridium complex. Specific examples of these cyclometalated iridium complexes are described, for example, in JP 2007-224025 A, JP 2006-290891 A, JP 2006-213723 A, JP 2006-111623 A, JP 2006-104201 A, JP 2006-063080 A, JP 2009-541431 W, JP 2009-526071 W, JP 2008-505076 W, JP 2007-513159 W, JP 2007-513158 W, JP 2002-540572 W, JP 2009-544167 W, JP 2009-522228 W, JP 2008-514005 W, JP 2008-504342 W, JP 2007-504272 W, JP 2006-523231 W, JP 2005-516040 W, WO 2010/086089.

In addition, triscyclometalated iridium complexes can be classified into homoleptic iridium complexes in which three cyclometalated ligands are the same (e.g. compound of general formula (2)) and heteroleptic iridium complexes in which all of three cyclometalated ligands are not the same (e.g. compound of general formula (4)). In the present invention, either a homoleptic iridium complex or a heteroleptic iridium complex can be produced as a triscyclometalated iridium complex. When the same aromatic heterocyclic bidentate ligands are introduced for producing a homoleptic iridium complex, non-halogenated iridium having a conjugated base of a strong acid as a ligand can be reacted with a single aromatic heterocyclic bidentate ligand to obtain an iridium complex. On the other hand, when different aromatic heterocyclic bidentate ligands are introduced for producing a heteroleptic iridium complex, non-halogenated iridium having a conjugated base of a strong acid as a ligand may be reacted with a plurality of kinds of aromatic heterocyclic bidentate ligands, or non-halogenated iridium having a conjugated base of a strong acid as a ligand can be reacted with an aromatic heterocyclic bidentate ligand, followed by reacting the reaction product with a different aromatic heterocyclic bidentate ligand to obtain a desired iridium complex. In the present invention, when a homoleptic iridium complex and a heteroleptic iridium complex are generated at the same time, these complexes can be separated and purified by column chromatography, and isolated from each other.

In addition, the present invention is also useful for production of a biscyclometalated iridium complex, and here, non-halogenated iridium having a conjugated base of a strong acid as a ligand can be reacted with an aromatic heterocyclic bidentate ligand, followed by reacting the reaction product with an auxiliary ligand (β-diketone ligand, picolinic acid ligand or the like) to obtain an iridium complex.

Examples of cyclometalated iridium complexes that can be produced by the method of the present invention are shown below.

[Chemical Formula 21]

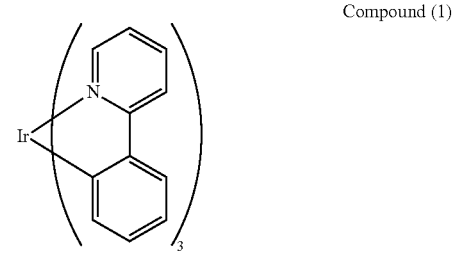

Compound (1)

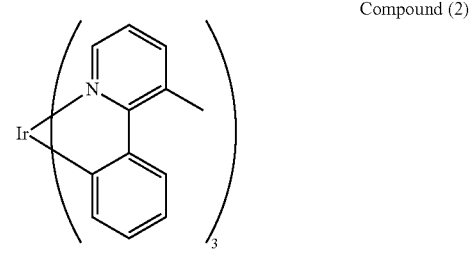

Compound (2)

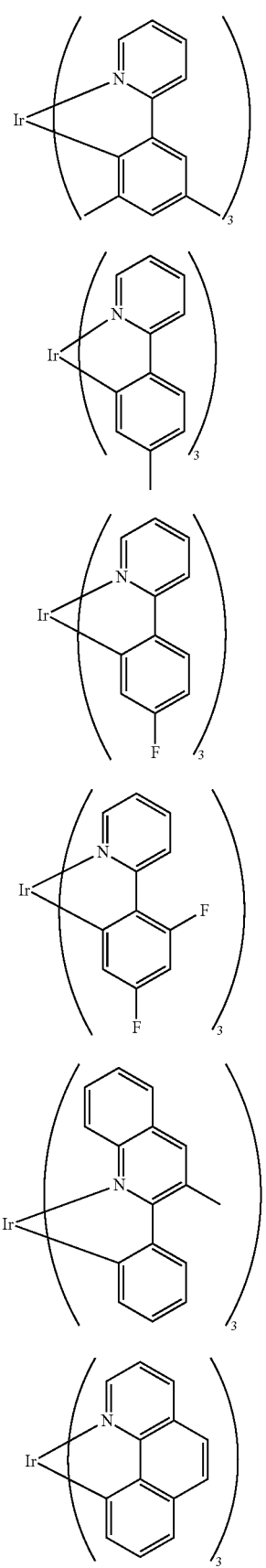

Compound (15)
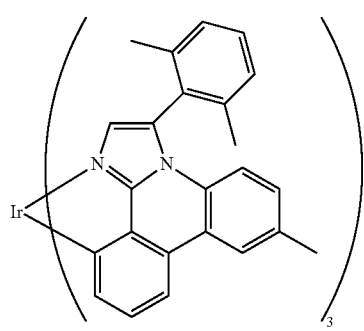
Compound (16)
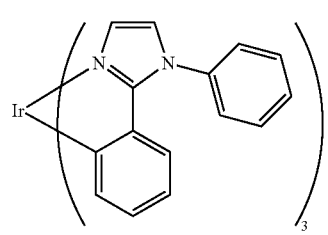
Compound (17)
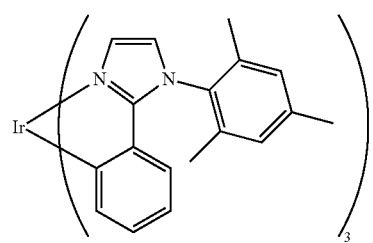
Compound (18)
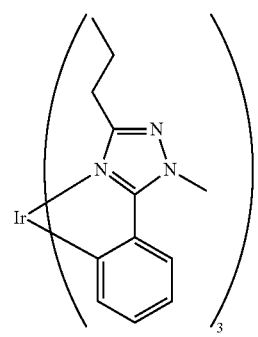
Compound (19)
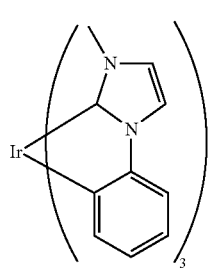
Compound (20)
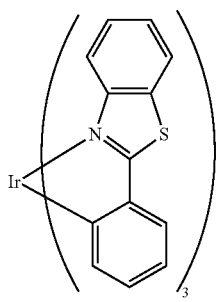
[Chemical Formula 22]
Compound (21)
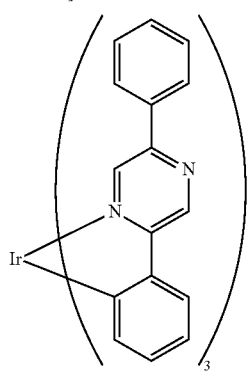
Compound (22)
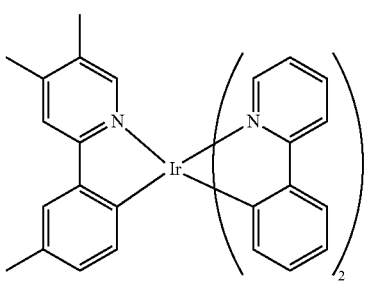
Compound (23)
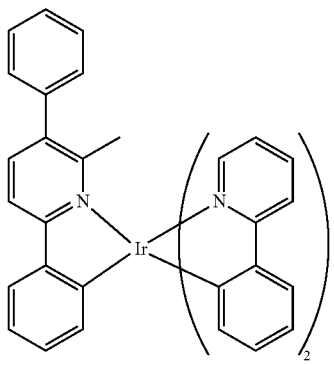
Compound (24)
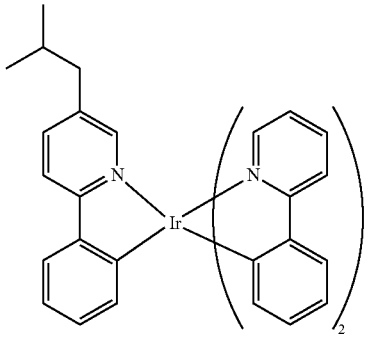

Compound (25)
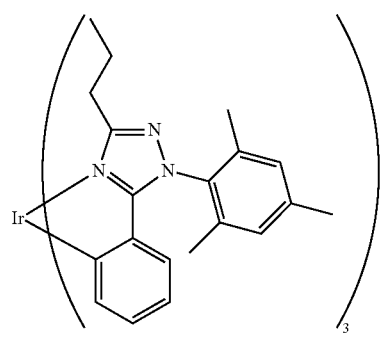
Compound (26)
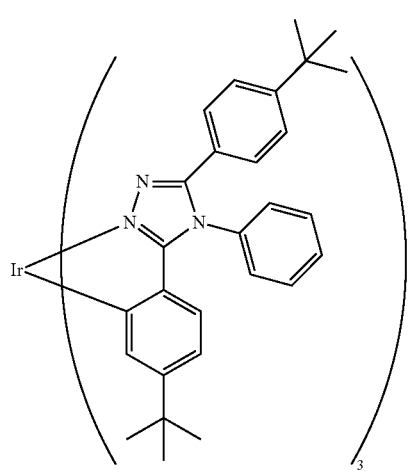
Compound (27)
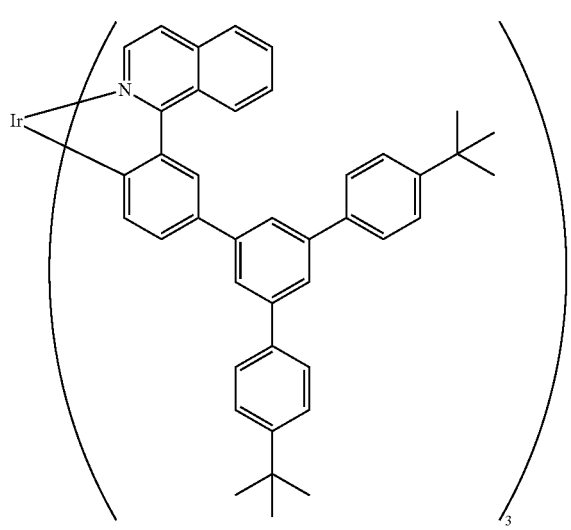
Compound (28)
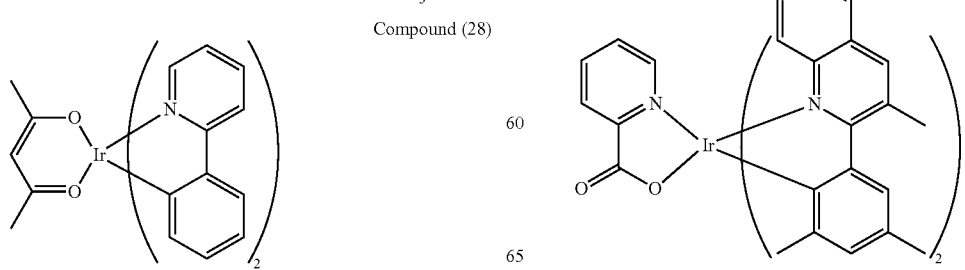
Compound (29)
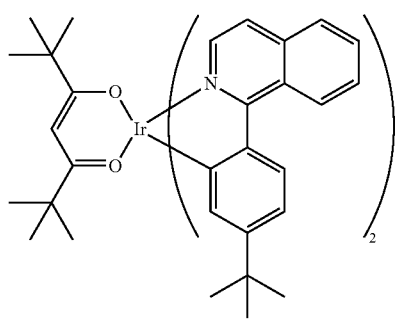
Compound (30)
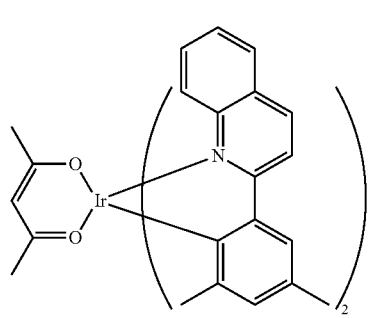
Compound (31)
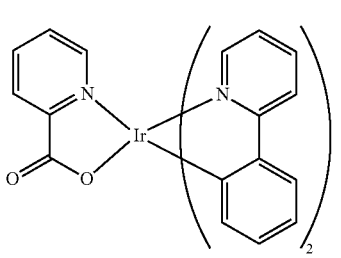
Compound (32)
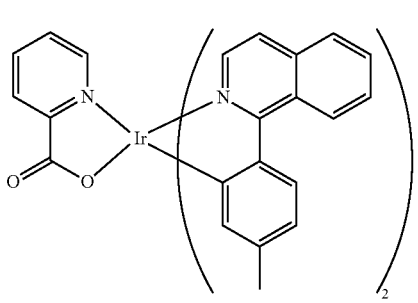
Compound (33)

[Chemical Formula 23]

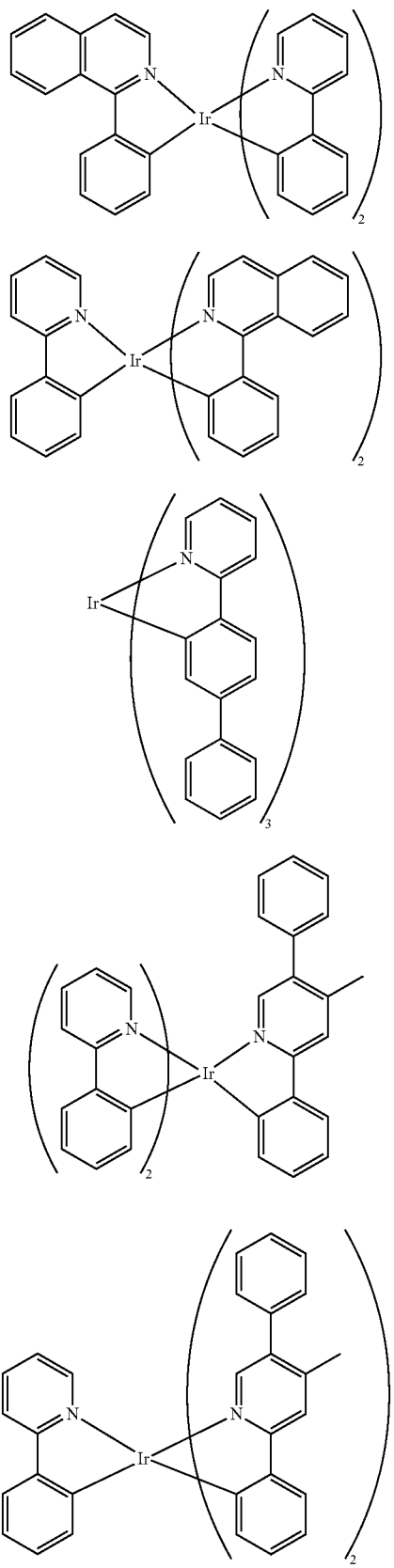

Compound (34)

Compound (35)

Compound (36)

Compound (37)

Compound (38)

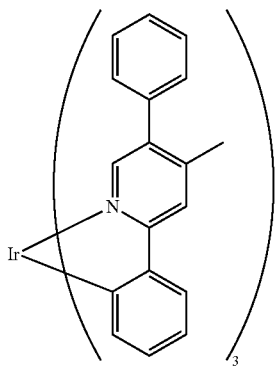

Compound (39)

As described above, the present invention is particularly useful for production of a triscyclometalated iridium complex. Here, the triscyclometalated iridium complex has a steric structure in which three β-diketone ligands are in octahedral arrangement around the iridium metal. With this steric structure, two kinds of geometric isomers, i.e. a facial isomer and a meridional isomer are present for the triscyclometalated iridium complex. A facial isomer and a meridional isomer are named by the nomenclature for isomers of a hexadentate octahedral complex and described in "Yuki-Kinzoku Kagaku—Kiso to Oyo (Organometal Chemistry—Basis and Application)", Akio Yamamoto (Shokabo Publishing Co., Ltd.), p. 143.

As described above, the facial isomer has high light-emitting efficiency, thus being desirable as a light-emitting material. In the present invention, a triscyclometalated iridium complex as a facial isomer can be efficiently produced by using non-halogenated iridium having a conjugated base of a strong acid as a ligand. The reason for this has not been evident yet, but the opinion of the present inventors is as follows.

That is, a cyclometalated iridium complex as a facial isomer is more advantageous from a thermodynamic point of view than a meridional isomer, and is easily generated by a high-temperature reaction. On the other hand, it is known that a cyclometalated iridium complex as a meridional isomer is advantageous from a kinetic point of view, and is easily generated by a low-temperature reaction. In a conventional art using iridium acetate as an iridium raw material as described above, a meridional isomer that is advantageous from a kinetic point of view may be easily generated because an acetic acid ligand is easily desorbed at a low temperature. On the other hand, when non-halogenated iridium having a conjugated base of a strong acid as a ligand is used as in the present invention, generation of a meridional isomer that is advantageous from a kinetic point of view may be suppressed due to the effect of a strong acid such as nitric acid. Generation of a facial isomer may be accelerated as generation of the meridional isomer is suppressed.

A geometric isomer in the cyclometalated iridium complex can be identified by analysis with various kinds of devices, such as $^1$H-NMR. The content of each of a facial isomer and a meridional isomer can be quantitatively determined by $^1$H-NMR, high-performance liquid chromatography or the like.

However, the present invention is not limited to production of a triscyclometalated iridium complex and a biscyclometalated iridium complex. The present invention has not only an advantage that a triscyclometalated iridium complex as a facial isomer can be efficiently produced, but also an advantage that a cyclometalated iridium complex free from a remaining halogen can be produced at a relatively low temperature. It is possible to have these advantages in production of a cyclometalated iridium complex other than a triscyclometalated iridium complex.

Advantageous Effects of the Invention

It is known that when previously known halogenated iridium (iridium chloride, iridium bromide or the like) is used, a desired cyclometalated iridium complex cannot be efficiently produced. This is mainly because a stable halogen-crosslinked dimer is generated.

On the other hand, in the present invention, non-halogenated iridium having a conjugated base of a strong acid as a ligand, unlike conventional halogenated iridium, is used, so that a halogen-crosslinked dimer is not generated at all, and thus a desired cyclometalated iridium complex can be efficiently produced. In addition, the cyclometalated iridium complex obtained by use of the present invention does not contain a halogen (chlorine or the like) derived from an iridium raw material. When a light-emitting layer or a plurality of organic compound layers including the light-emitting layer in a light-emitting device contain an iridium complex produced in the present invention, a light-emitting device superior in light-emitting efficiency and durability to a conventional light-emitting device can be obtained.

In addition, in the present invention, a cyclometalated iridium complex can be produced under more gentle conditions as compared to a case where tris(2,4-pentanedionato) iridium(III) is used.

Further, in the present invention, a triscyclometalated iridium complex as a facial isomer, which is useful as a phosphorescent material, can be more efficiently produced as compared to a conventional method using iridium acetate.

DESCRIPTION OF EMBODIMENTS

Hereinafter, an embodiment of the present invention will be described in detail, but the embodiment is illustrative, and the present invention is not limited thereto. In this embodiment, iridium nitrate or iridium sulfate was used as non-halogenated iridium having a conjugated base of a strong acid as a ligand, and a plurality of kinds of aromatic heterocyclic bidentate ligands were reacted to produce cyclometalated iridium complexes (compounds (1), (4), (5), (10), (12), (14) and (16) among iridium compounds listed in Chemical Formula 21 and compounds (34) to (39) in Chemical Formula 23).

Iridium nitrate serving as an iridium raw material for the cyclometalated iridium complex in this embodiment was obtained as a black solid by performing synthesis in accordance with JP 2001-106536 A, then distilling off nitric acid under reduced pressure, and drying and solidifying the resulting product. The black solid of iridium nitrate was dissolved by adding water thereto, and thus an iridium nitrate aqueous solution was prepared. The iridium nitrate aqueous solution had a pH of 0.54. The concentration of remaining chlorine contained in the iridium nitrate aqueous solution was 160 ppm. The iridium nitrate aqueous solution was used in Examples 1 to 16 and 19. The thus-prepared black solid of iridium nitrate was used in Examples 17 and 18.

In this embodiment, the following compounds (A) to (I) were used as aromatic heterocyclic bidentate ligands. Hereinafter, examples will be described.

[Chemical Formula 24]

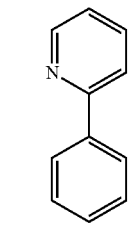

Compound (A)

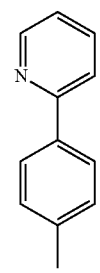

Compound (B)

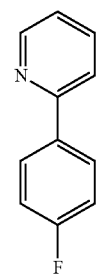

Compound (C)

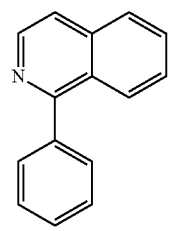

Compound (D)

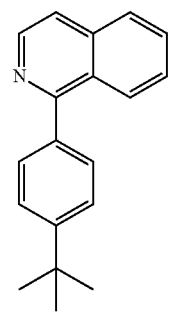

Compound (E)

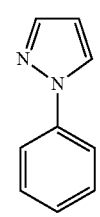

Compound (F)

-continued

Compound (G)

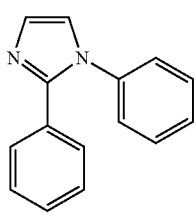

Compound (H)

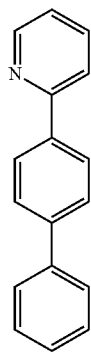

Compound (I)

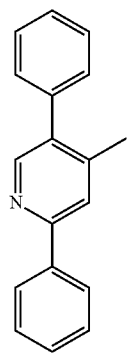

<Example 1> Synthesis of Compound (1)

403.8 mg of an iridium nitrate aqueous solution (iridium content: 9.52 wt %), 186.2 mg of compound (A) and 5 ml of ethylene glycol were reacted by heating in an argon atmosphere at 180° C. for 17 hours. The reaction mixture was cooled to room temperature, and methanol was added. The precipitated solid was collected by filtration, and washed with methanol. The compound was identified by $^1$H-NMR, and confirmed to be compound (1). The isolated yield of compound (1) was 78%.

<Example 2> Synthesis of Compound (4)

403.8 mg of an iridium nitrate aqueous solution (iridium content: 9.52 wt %), 203.1 mg of compound (B) and 5 ml of ethylene glycol were reacted by heating in an argon atmosphere at 180° C. for 17 hours. The reaction mixture was cooled to room temperature, and extracted with dichloromethane added thereto. The oil extract was collected, and concentrated under reduced pressure, and the thus-obtained solid was recrystallized with dichloromethane and methanol. The compound was identified by $^1$H-NMR, and confirmed to be compound (4). The isolated yield of compound (4) was 70%.

<Example 3> Synthesis of Compound (5)

403.8 mg of an iridium nitrate aqueous solution (iridium content: 9.52 wt %), 207.8 mg of compound (C) and 5 ml of ethylene glycol were reacted by heating in an argon atmosphere at 180° C. for 17 hours. The reaction mixture was cooled to room temperature, and methanol was added. The precipitated solid was collected by filtration, and washed with methanol. The resulting product was purified by silica gel column chromatography (eluant: dichloromethane). The compound was identified by $^1$H-NMR, and confirmed to be compound (5). The isolated yield of compound (5) was 75%.

<Example 4> Synthesis of Compound (10)

403.8 mg of an iridium nitrate aqueous solution (iridium content: 9.52 wt %), 246.3 mg of compound (D) and 5 ml of ethylene glycol were reacted by heating in an argon atmosphere at 180° C. for 17 hours. The reaction mixture was cooled to room temperature, and methanol was added. The precipitated solid was collected by filtration, and washed with methanol. The compound was identified by $^1$H-NMR, and confirmed to be compound (10). The isolated yield of compound (10) was 80%.

<Example 5> Synthesis of Compound (12)

403.8 mg of an iridium nitrate aqueous solution (iridium content: 9.52 wt %), 313.6 mg of compound (E) and 5 ml of ethylene glycol were reacted by heating in an argon atmosphere at 180° C. for 17 hours. The reaction mixture was cooled to room temperature, and methanol was added. The precipitated solid was collected by filtration, and washed with methanol. The compound was identified by $^1$H-NMR, and confirmed to be compound (12). The isolated yield of compound (12) was 75%.

<Example 6> Synthesis of Compound (14)

403.8 mg of an iridium nitrate aqueous solution (iridium content: 9.52 wt %), 173.0 mg of compound (F) and 5 ml of ethylene glycol were reacted by heating in an argon atmosphere at 180° C. for 17 hours. The reaction mixture was cooled to room temperature, and methanol was added. The precipitated solid was collected by filtration, and washed with methanol. The compound was identified by $^1$H-NMR, and confirmed to be compound (14). The isolated yield of compound (12) was 65%.

<Example 7> Synthesis of Compound (16)

807.6 mg of an iridium nitrate aqueous solution (iridium content: 9.52 wt %), 528.0 mg of compound (G) and 5 ml of ethylene glycol were reacted by heating in an argon atmosphere at 180° C. for 17 hours. The reaction mixture was cooled to room temperature, and methanol was added. The precipitated solid was collected by filtration, and washed with methanol. The compound was identified by $^1$H-NMR, and confirmed to be compound (16). The isolated yield of compound (16) was 60%.

<Example 8> Synthesis of Compound (36)

403.8 mg of an iridium nitrate aqueous solution (iridium content: 9.52 wt %), 277.6 mg of compound (H) and 5 ml of ethylene glycol were reacted by heating in an argon atmosphere at 180° C. for 17 hours. The reaction mixture was cooled to room temperature, and methanol was added. The precipitated solid was collected by filtration, and washed with methanol. The compound was identified by ¹H-NMR, and confirmed to be compound (36). The isolated yield of compound (36) was 80%.

<Example 9> Synthesis of Compound (39)

403.8 mg of an iridium nitrate aqueous solution (iridium content: 9.52 wt %), 294.4 mg of compound (I) and 5 ml of ethylene glycol were reacted by heating in an argon atmosphere at 180° C. for 17 hours. The reaction mixture was cooled to room temperature, and methanol was added. The precipitated solid was collected by filtration, and washed with methanol. Further, the resulting product was purified by silica gel column chromatography (eluant: dichloromethane). The compound was identified by ¹H-NMR, and confirmed to be compound (39). The isolated yield of compound (39) was 70%.

<Example 10> Synthesis of Compound (1)

403.8 mg of an iridium nitrate aqueous solution (iridium content: 9.52 wt %), 186.2 mg of compound (A) and 5 ml of ethylene glycol were reacted by heating in an argon atmosphere at 150° C. for 34 hours. The reaction mixture was cooled to room temperature, and methanol was added. The precipitated solid was collected by filtration, and washed with methanol. The compound was identified by ¹H-NMR, and confirmed to be compound (1). The isolated yield of compound (1) was 70%.

<Example 11> Synthesis of Compound (1)

403.8 mg of an iridium nitrate aqueous solution (iridium content: 9.52 wt %) was diluted by a factor of 10 by adding water thereto, and 186.2 mg of compound (A) and 50 ml of ethylene glycol were then reacted by heating in an argon atmosphere at 180° C. for 17 hours. The reaction mixture was cooled to room temperature, and methanol was added. The precipitated solid was collected by filtration, and washed with methanol. The compound was identified by ¹H-NMR, and confirmed to be compound (1). The isolated yield of compound (1) was 60%.

<Example 12> Synthesis of Compound (1)

403.8 mg of an iridium nitrate aqueous solution (iridium content: 9.52 wt %), 186.2 mg of compound (A) and 5 ml of diethylene glycol were reacted by heating in an argon atmosphere at 180° C. for 17 hours. The reaction mixture was cooled to room temperature, and methanol was added. The precipitated solid was collected by filtration, and washed with methanol. The compound was identified by ¹H-NMR, and confirmed to be compound (1). The isolated yield of compound (1) was 60%.

<Example 13> Synthesis of Compound (1)

403.8 mg of an iridium nitrate aqueous solution (iridium content: 9.52 wt %) was weighed, the solution was distilled off under reduced pressure by an evaporator, and 186.2 mg of compound (A) and 5 ml of diethylene glycol were then added, and reacted by heating in an argon atmosphere at 180° C. for 17 hours. The reaction mixture was cooled to room temperature, and methanol was added. The precipitated solid was collected by filtration, and washed with methanol. The compound was identified by ¹H-NMR, and confirmed to be compound (1). The isolated yield of compound (1) was 75%.

<Example 14> Synthesis of Compounds (1), (34) and (35)

403.8 mg of an iridium nitrate aqueous solution (iridium content: 9.52 wt %), 93.1 mg of compound (A), 123.2 mg of compound (D) and 5 ml of ethylene glycol were reacted by heating in an argon atmosphere at 180° C. for 17 hours. The reaction mixture was cooled to room temperature, and methanol was added. The precipitated solid was collected by filtration, and washed with methanol. The yield of the resulting solid was 102 mg. Analysis was performed by HPLC (Prominence manufactured by Shimadzu Corporation, column: normal phase silica gel, mobile phase: mixed solvent of THF (40%) and hexane (60%), detection wavelength: 300 nm), and the result showed that the production ratios of compounds (1), (34) and (35) were 84.1%, 15.2% and 0.7% (peak area ratio), respectively.

<Example 15> Synthesis of Compounds (1), (10), (34) and (35)

403.8 mg of an iridium nitrate aqueous solution (iridium content: 9.52 wt %), 31.0 mg of compound (A), 205.3 mg of compound (D) and 5 ml of ethylene glycol were reacted by heating in an argon atmosphere at 180° C. for 17 hours. The reaction mixture was cooled to room temperature, and methanol was added. The precipitated solid was collected by filtration, and washed with methanol. The yield of the resulting solid was 110 mg. Analysis was performed by HPLC (Prominence manufactured by Shimadzu Corporation, column: normal phase silica gel, mobile phase: mixed solvent of THF (40%) and hexane (60%), detection wavelength: 300 nm), and the result showed that the production ratios of compounds (1), (10), (34) and (35) were 3.7%, 52.2%, 11.9% and 32.2% (peak area ratio), respectively.

<Example 16> Synthesis of Compounds (1), (37), (38) and (39)

807.6 mg of an iridium nitrate aqueous solution (iridium content: 9.52 wt %), 124 mg of compound (A), 98 mg of compound (I) and 5 ml of ethylene glycol were reacted by heating in an argon atmosphere at 180° C. for 17 hours. The reaction mixture was cooled to room temperature, and then extracted with dichloromethane added thereto. The organic extract was concentrated under reduced pressure, and from the precipitated solid, origin impurities were removed by silica gel chromatography (eluant: dichloromethane). The yield of the solid obtained after purification was 196 mg. Analysis was performed by HPLC (Prominence manufactured by Shimadzu Corporation, column: normal phase silica gel, mobile phase: mixed solvent of THF (40%) and hexane (60%), detection wavelength: 300 nm), and the result showed that the production ratios of compounds (1), (37), (38) and (39) were 17.9%, 40.6%, 31.8% and 9.7% (peak area ratio), respectively.

<Example 17> Synthesis of Compound (1)

71.9 mg of a black solid of iridium nitrate (iridium content: 53.48 wt %), 109.0 mg of compound (A) and 5 ml of ethylene glycol were reacted by heating in an argon atmosphere at 180° C. for 17 hours. The reaction mixture was cooled to room temperature, and methanol was added. The precipitated solid was collected by filtration, and washed with methanol. Further, origin impurities were removed by silica gel chromatography (eluant: dichloromethane) to obtain a yellow solid. The compound was identified by $^1$H-NMR, and confirmed to be compound (1). The isolated yield of compound (1) was 93%.

<Example 18> Synthesis of Compound (10)

71.0 mg of a black solid of iridium nitrate (iridium content: 54.12 wt %), 143.5 mg of compound (D) and 5 ml of ethylene glycol were reacted by heating in an argon atmosphere at 180° C. for 17 hours. The reaction mixture was cooled to room temperature, and methanol was added. The precipitated solid was collected by filtration, and washed with methanol. Further, origin impurities were removed by silica gel chromatography (eluant: dichloromethane) to obtain a red solid. The compound was identified by $^1$H-NMR, and confirmed to be compound (10). The isolated yield of compound (10) was 73%.

<Example 19> Synthesis of Compounds (1), (37), (38) and (39)

807.6 mg of an iridium nitrate aqueous solution (iridium content: 9.52 wt %), 248 mg of compound (A), 196 mg of compound (I) and 15 ml of ethylene glycol were reacted by heating in an argon atmosphere at 180° C. for 17 hours. The reaction mixture was cooled to room temperature, and then extracted with dichloromethane added thereto. The organic extract was concentrated under reduced pressure, and from the precipitated solid, origin impurities were removed by silica gel chromatography (eluant: dichloromethane). The yield of the solid obtained after purification was 236 mg. Analysis was performed by HPLC (Prominence manufactured by Shimadzu Corporation, column: normal phase silica gel, mobile phase: mixed solvent of THF (40%) and hexane (60%), detection wavelength: 300 nm), and the result showed that the production ratios of compounds (1), (37), (38) and (39) were 17.3%, 68.5%, 8.4% and 5.8% (peak area ratio), respectively.

<Comparative Example 1> Synthesis of Compound (1)

In place of the iridium nitrate aqueous solution in Example 1, tris(2,4-pentanedionato)iridium (III) as a conventional iridium raw material was used to similarly carry out a reaction. However, compound (1) was not obtained.

<Comparative Example 2> Synthesis of Compound (1)

In place of the iridium nitrate aqueous solution in Example 1, an iridium chloride (III) n-hydrate was used to carry out a reaction, but a chlorine-crosslinked dimer was obtained, and compound (1) was not obtained.

<Comparative Example 3> Synthesis of Compound (10)

In place of the iridium nitrate aqueous solution in Example 4, tris(2,4-pentanedionato)iridium (III) as a conventional iridium raw material was used to carry out a reaction. However, compound (10) was not obtained.

<Comparative Example 4> Synthesis of Compound (10)

In place of the iridium nitrate aqueous solution in Example 4, an iridium chloride (III) n-hydrate was used to carry out a reaction, but a chlorine-crosslinked dimer was obtained, and compound (10) was not obtained.

The results of examination in Examples 1 to 19 as described above revealed that it was possible to produce a cyclometalated iridium complex by using non-halogenated iridium having a conjugated base of a strong acid as a ligand or an aqueous solution thereof. In addition, it was confirmed that in this embodiment, not only a homoleptic iridium complex such as compound (1) was produced singly (Examples 1 to 13, 17 and 18), but also a homoleptic iridium complex and a heteroleptic iridium complex were produced at the same time by reacting a plurality of aromatic heterocyclic bidentate ligands with non-halogenated iridium having a conjugated base of a strong acid as a ligand (Examples 14 to 16 and 19).

The results of analysis by $^1$H-NMR showed that various kinds of cyclometalated iridium complexes synthesized in Examples 1 to 19 were each substantially composed of a facial isomer, and little meridional isomer was detected in these cyclometalated iridium complexes.

On the other hand, in Comparative Examples 1 and 3, tris(2,4-pentanedionato)iridium (III) as a conventional iridium raw material was used, and it was not possible to produce a cyclometalated iridium complex (compound (1) or (10)). This may be because in synthesis conditions in this embodiment, the reaction temperature was set to 200° C. or lower (180° C.). When tris(2,4-pentanedionato)iridium (III) is applied, it is necessary to set the reaction temperature to 200° C. or higher. As shown in Examples 1 to 16, it was revealed that by using non-halogenated iridium having a conjugated base of a strong acid as a ligand, a desired cyclometalated iridium complex was produced with a high yield even when the reaction temperature was 200° C. or lower (150 to 180° C.).

In addition, in Comparative Examples 2 and 4, iridium chloride (III) as a conventional iridium raw material was used, and it was revealed that a desired cyclometalated iridium complex was not obtained. This is ascribable to influences of generation of a chlorine-crosslinked dimer. It was confirmed that by using a non-halogen (non-chlorine) raw material as in each example, a desired cyclometalated iridium complex was produced without generating a chlorine-crosslinked dimer.

Next, the purity of the facial isomer of the cyclometalated iridium complex as a product was precisely analyzed by HPLC, and the result of the analysis was examined while being compared to that in the case where iridium acetate was used as an iridium raw material. In addition, examination was similarly conducted for the case where iridium sulfate was used as non-halogenated iridium having a conjugated base of a strong acid as a ligand.

Example 20

Compound (1) obtained in Example 1 was analyzed by HPLC (Prominence manufactured by Shimadzu Corporation, column: normal phase silica gel, mobile phase: mixed solvent of THF (40%) and hexane (60%), detection wavelength: 300 nm), and the result showed that the production ratio of a facial isomer and a meridional isomer was 99.64: 0.36 (peak area ratio).

Example 21

Compound (10) obtained in Example 4 was analyzed by HPLC (Prominence manufactured by Shimadzu Corporation, column: normal phase silica gel, mobile phase: mixed solvent of THF (40%) and hexane (60%), detection wavelength: 300 nm), and the result showed that the production ratio of a facial isomer and a meridional isomer was 99.57:0.43 (peak area ratio).

<Example 22> Synthesis of Compound (1) with Iridium Sulfate

Except that an iridium sulfate (IV) n-hydrate was used in place of the iridium nitrate aqueous solution used in Example 1, the same procedure as in Example 1 was carried out to produce compound (1). The iridium sulfate (IV) n-hydrate used is a commercially available product (selling source: Mitsuwa Chemicals Co., Ltd.). Compound (1) obtained was analyzed by HPLC (Prominence manufactured by Shimadzu Corporation, column: normal phase silica gel, mobile phase: mixed solvent of THF (40%) and hexane (60%), detection wavelength: 300 nm), and the result showed that the production ratio of a facial isomer and a meridional isomer was 99.97:0.03 (peak area ratio).

Comparative Example 5

A reaction was carried out in the same manner as in Example 1 except that iridium acetate (manufactured by ChemPur GmbH) was used in place of the iridium nitrate aqueous solution in Example 1. The compound was identified by $^1$H-NMR, and confirmed to be compound (1). The isolated yield of compound (1) was 75%. Compound (1) obtained was analyzed by HPLC (Prominence manufactured by Shimadzu Corporation, column: normal phase silica gel, mobile phase: mixed solvent of THF (40%) and hexane (60%), detection wavelength: 300 nm), and the result showed that the production ratio of a facial isomer and a meridional isomer was 83.59:16.41 (peak area ratio).

Comparative Example 6

A reaction was carried out in the same manner as in Example 4 except that iridium acetate (manufactured by ChemPur GmbH) was used in place of the iridium nitrate aqueous solution in Example 4. The compound was identified by $^1$H-NMR, and confirmed to be compound (10). The isolated yield of compound (10) was 75%. Compound (10) obtained was analyzed by HPLC (Prominence manufactured by Shimadzu Corporation, column: normal phase silica gel, mobile phase: mixed solvent of THF (40%) and hexane (60%), detection wavelength: 300 nm), and the result showed that the production ratio of a facial isomer and a meridional isomer was 99.24:0.76 (peak area ratio).

Comparison of Example 20 with Comparative Example 5 shows that the purity of the facial isomer of compound (1) is higher in the production method of Example 20. In addition, a cyclometalated iridium complex containing a high-purity facial isomer can also be obtained by using an iridium sulfate (IV) n-hydrate as in Example 22. Similarly, comparison of Example 21 with Comparative Example 6 shows that the purity of the facial isomer of compound (10) is higher in the production method of Example 21.

INDUSTRIAL APPLICABILITY

The present invention makes it possible to more efficiently obtain a cyclometalated iridium complex as a facial isomer as compared to a case where a previously known iridium raw material is used, and thus the present invention contributes to production of a phosphorescent material that can be suitably used for an organic EL device etc.

The invention claimed is:

1. A method for producing a cyclometalated iridium complex, the method comprising producing a cyclometalated iridium complex by reacting a raw material including an iridium compound with an aromatic heterocyclic bidentate ligand capable of forming an iridium-carbon bond,
   wherein the raw material to be reacted is non-halogenated iridium having a conjugated base of a strong acid as a ligand, and
   wherein the non-halogenated iridium is iridium nitrate or iridium sulfate.

2. The method for producing a cyclometalated iridium complex according to claim 1, wherein the ligand of the non-halogenated iridium is a conjugated base of a strong acid having a pKa of 3 or less.

3. The method for producing a cyclometalated iridium complex according to claim 1, wherein the non-halogenated iridium is in a solid state.

4. The method for producing a cyclometalated iridium complex according to claim 1, wherein the non-halogenated iridium is dissolved or dispersed in a solvent.

5. The method for producing a cyclometalated iridium complex according to claim 4, wherein the pH of the solution containing non-halogenated iridium is in a range of 0 to 3.

6. The method for producing a cyclometalated iridium complex according to claim 1, wherein the cyclometalated iridium complex is a biscyclometalated iridium complex or a triscyclometalated iridium complex.

7. The method for producing a cyclometalated iridium complex according to claim 1, wherein at least one of a homoleptic triscyclometalated iridium complex and a heteroleptic triscyclometalated iridium complex is produced as a cyclometalated iridium complex.

8. The method according to claim 1, wherein a cyclometalated iridium complex represented by the general formula (2) is produced by reacting non-halogenated iridium having a conjugated base of a strong acid as a ligand with an aromatic heterocyclic bidentate ligand represented by the general formula (1):

[Chemical Formula 1]

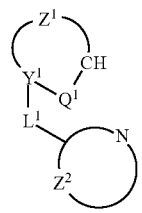

General formula (1)

[Chemical Formula 2]

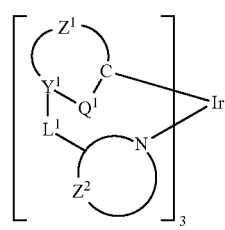

General formula (2)

(in general formulae (1) and (2), N represents a nitrogen atom; C represents a carbon atom; $Z^1$ and $Z^2$ each independently represent a nonmetal atom group necessary for forming a 5- or 6-membered ring; the formed ring may further form a fused ring with another ring; $L^1$ represents a single bond or a divalent group; $Y^1$ represents a nitrogen atom or a carbon atom; $Q^1$ represents a linkage of a carbon atom with $Y^1$ through a single bond when $Y^1$ is a nitrogen atom; $Q^1$ represents a linkage of a carbon atom with $Y^1$ through a double bond when $Y^1$ is a carbon atom).

9. The method according to claim 1, wherein a cyclometalated iridium complex represented by the general formula (4) is produced by reacting non-halogenated iridium having a conjugated base of a strong acid as a ligand, an aromatic heterocyclic bidentate ligand represented by the general formula (1) and an aromatic heterocyclic bidentate ligand represented by the general formula (3):

[Chemical Formula 3]

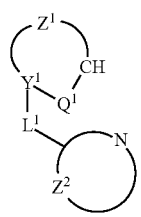

General formula (1)

[Chemical Formula 4]

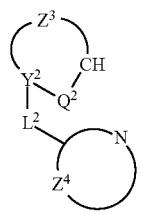

General formula (3)

[Chemical Formula 5]

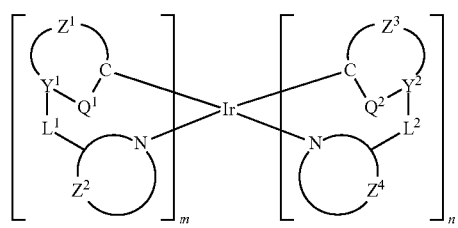

General formula (4)

(in general formulae (3) and (4), N represents a nitrogen atom; C represents a carbon atom; $Z^1$ and $Z^2$ each independently represent a nonmetal atom group necessary for forming a 5- or 6-membered ring; the formed ring may further form a fused ring with another ring; $L^1$ represents a single bond or a divalent group; $Y^1$ represents a nitrogen atom or a carbon atom; $Q^1$ represents a linkage of a carbon atom with $Y^1$ through a single bond when $Y^1$ is a nitrogen atom; $Q^1$ represents a linkage of a carbon atom with $Y^1$ through a double bond when $Y^1$ is a carbon atom; $Z^3$ and $Z^4$ each independently represent a nonmetal atom group necessary for forming a 5- or 6-membered ring; the formed ring may further form a fused ring with another ring; $L^2$ represents a single bond or a divalent group; $Y^2$ represents a nitrogen atom or a carbon atom; $Q^2$ represents a linkage of a carbon atom with $Y^2$ through a single bond when $Y^2$ is a nitrogen atom; $Q^2$ represents a linkage of a carbon atom with $Y^2$ through a double bond when $Y^2$ is a carbon atom; the aromatic heterocyclic bidentate ligand represented by the general formula (1) is not identical to the aromatic heterocyclic bidentate ligand represented by the general formula (3); and m is 1 or 2, and n is 1 or 2, with the proviso that m+n=3).

10. The method for producing a cyclometalated iridium complex according to claim 1, wherein the aromatic heterocyclic bidentate ligand is at least one of compounds represented by the following formulae:

[Chemical Formula 6]

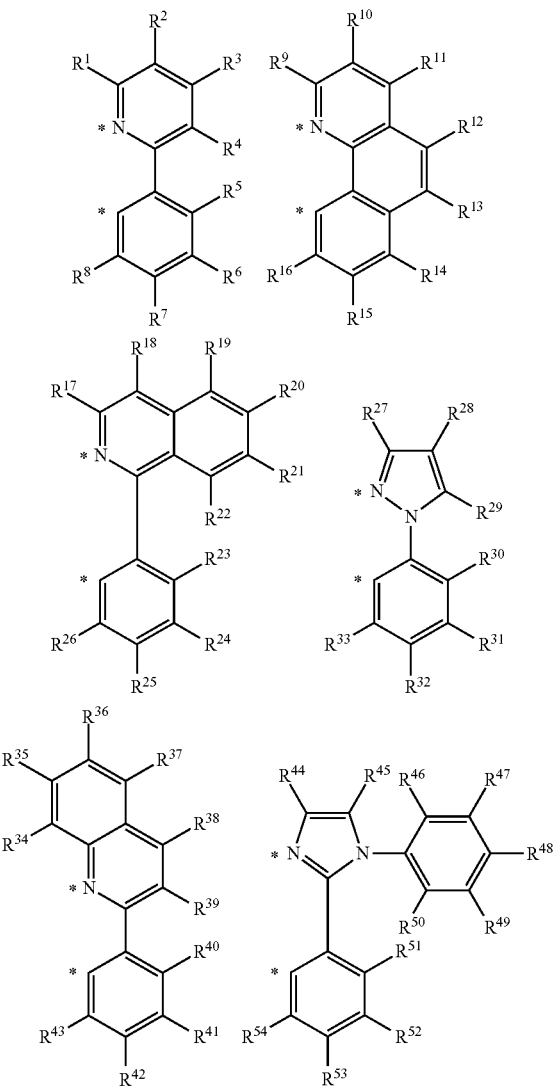

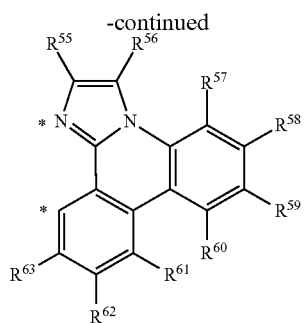

(wherein $R^1$ to $R^{73}$ each independently represent a hydrogen atom or a substituent; adjacent ones of $R^1$ to $R^{73}$ may be linked together to form a ring structure; and * represents a binding site with iridium).

11. The method for producing a cyclometalated iridium complex according to claim 2, wherein the non-halogenated iridium is iridium nitrate or iridium sulfate.

12. The method for producing a cyclometalated iridium complex according to claim 2, wherein the non-halogenated iridium is in a solid state.

13. The method for producing a cyclometalated iridium complex according to claim 2, wherein the non-halogenated iridium is in a solid state.

14. The method for producing a cyclometalated iridium complex according to claim 2, wherein the non-halogenated iridium is dissolved or dispersed in a solvent.

15. The method for producing a cyclometalated iridium complex according to claim 2, wherein the cyclometalated iridium complex is a biscyclometalated iridium complex or a triscyclometalated iridium complex.

16. The method for producing a cyclometalated iridium complex according to claim 2, wherein at least one of a homoleptic triscyclometalated iridium complex and a heteroleptic triscyclometalated iridium complex is produced as a cyclometalated iridium complex.

17. The method according to claim 2, wherein a cyclometalated iridium complex represented by the general formula (2) is produced by reacting non-halogenated iridium having a conjugated base of a strong acid as a ligand with an aromatic heterocyclic bidentate ligand represented by the general formula (1):

[Chemical Formula 1]

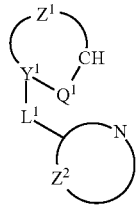

General formula (1)

[Chemical Formula 2]

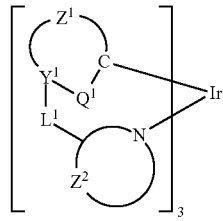

General formula (2)

(in general formulae (1) and (2), N represents a nitrogen atom; C represents a carbon atom; $Z^1$ and $Z^2$ each independently represent a nonmetal atom group necessary for forming a 5- or 6-membered ring; the formed ring may further form a fused ring with another ring; $L^1$ represents a single bond or a divalent group; $Y^1$ represents a nitrogen atom or a carbon atom; $Q^1$ represents a linkage of a carbon atom with $Y^1$ through a single bond when $Y^1$ is a nitrogen atom; $Q^1$ represents a linkage of a carbon atom with $Y^1$ through a double bond when $Y^1$ is a carbon atom).

18. The method according to claim 2, wherein a cyclometalated iridium complex represented by the general formula (4) is produced by reacting non-halogenated iridium having a conjugated base of a strong acid as a ligand, an aromatic heterocyclic bidentate ligand represented by the general formula (1) and an aromatic heterocyclic bidentate ligand represented by the general formula (3):

[Chemical Formula 3]

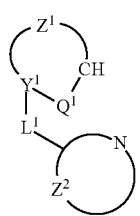

General formula (1)

[Chemical Formula 4]

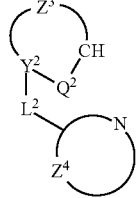

General formula (3)

-continued

[Chemical Formula 5]

General formula (4)

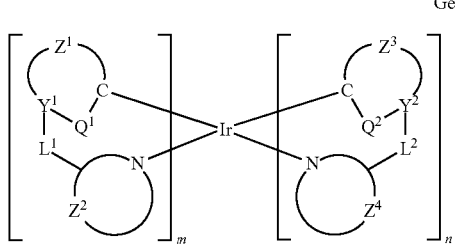

(in general formulae (3) and (4), N represents a nitrogen atom; C represents a carbon atom; $Z^1$ and $Z^2$ each independently represent a nonmetal atom group necessary for forming a 5- or 6-membered ring; the formed ring may further form a fused ring with another ring; $L^1$ represents a single bond or a divalent group; $Y^1$ represents a nitrogen atom or a carbon atom; $Q^1$ represents a linkage of a carbon atom with $Y^1$ through a single bond when $Y^1$ is a nitrogen atom; $Q^1$ represents a linkage of a carbon atom with $Y^1$ through a double bond when $Y^1$ is a carbon atom; $Z^3$ and $Z^4$ each independently represent a nonmetal atom group necessary for forming a 5- or 6-membered ring; the formed ring may further form a fused ring with another ring; $L^2$ represents a single bond or a divalent group; $Y^2$ represents a nitrogen atom or a carbon atom; $Q^2$ represents a linkage of a carbon atom with $Y^2$ through a single bond when $Y^2$ is a nitrogen atom; $Q^2$ represents a linkage of a carbon atom with $Y^2$ through a double bond when $Y^2$ is a carbon atom; the aromatic heterocyclic bidentate ligand represented by the general formula (1) is not identical to the aromatic heterocyclic bidentate ligand represented by the general formula (3); and m is 1 or 2, and n is 1 or 2, with the proviso that m+n=3).

19. The method for producing a cyclometalated iridium complex according to claim 2, wherein the aromatic heterocyclic bidentate ligand is at least one of compounds represented by the following formulae:

[Chemical Formula 6]

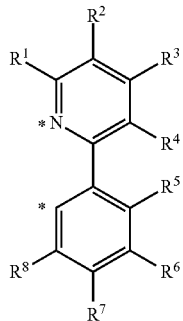

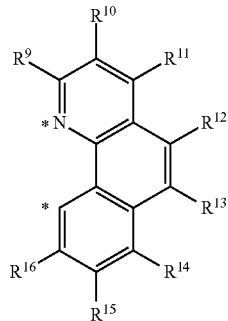

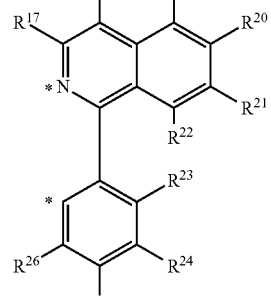

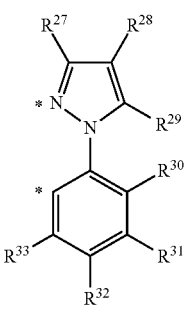

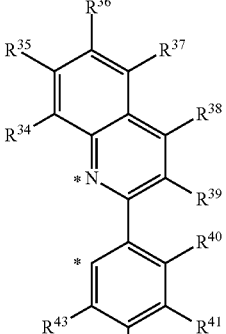

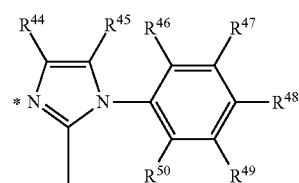

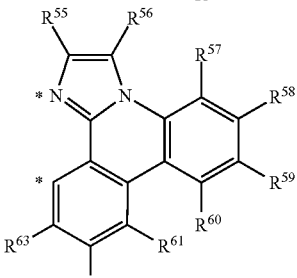

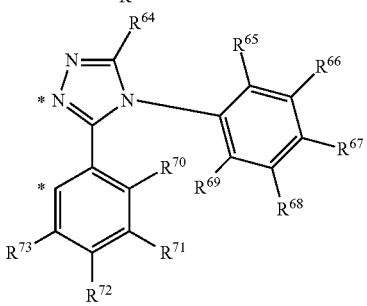

(wherein $R^1$ to $R^{73}$ each independently represent a hydrogen atom or a substituent; adjacent ones of $R^1$ to $R^{73}$ may be linked together to form a ring structure; and * represents a binding site with iridium).

* * * * *